1278319B2

(12) United States Patent
Harris et al.

(10) Patent No.: US 11,278,319 B2
(45) Date of Patent: Mar. 22, 2022

(54) EXPANDABLE MEDICAL DEVICE FOR USE WITH A NEEDLE

(71) Applicant: BOSTON SCIENTIFIC SCIMED, INC., Maple Grove, MN (US)

(72) Inventors: Colby Harris, Weston, MA (US); Paul Smith, Smithfield, RI (US); James Weldon, Newton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 236 days.

(21) Appl. No.: 16/507,836

(22) Filed: Jul. 10, 2019

(65) Prior Publication Data

US 2020/0015852 A1 Jan. 16, 2020

Related U.S. Application Data

(60) Provisional application No. 62/696,516, filed on Jul. 11, 2018.

(51) Int. Cl.
*A61B 17/34* (2006.01)
*A61B 10/04* (2006.01)
*A61M 25/00* (2006.01)

(52) U.S. Cl.
CPC .......... *A61B 17/3496* (2013.01); *A61B 10/04* (2013.01); *A61B 17/3478* (2013.01); *A61B 2010/045* (2013.01); *A61M 25/0074* (2013.01); *A61M 2025/0089* (2013.01)

(58) Field of Classification Search
CPC ...... A61M 2025/0089; A61M 25/0074; A61M 25/0084; A61B 17/3496; A61B 1/3478; A61B 17/3401; A61B 2090/0801; A61B 2090/08021; A61B 10/0233; A61B 10/02; A61B 2010/045

USPC .......................................................... 606/185
See application file for complete search history.

(56) References Cited

U.S. PATENT DOCUMENTS

| 7,413,540 | B2 | 8/2008 | Gellman et al. |
| 7,918,849 | B2 * | 4/2011 | Bleich .................. A61B 1/3135 606/32 |
| 8,357,104 | B2 | 1/2013 | Moos et al. |
| 2009/0118639 | A1 | 5/2009 | Moos et al. |
| 2009/0125036 | A1 | 5/2009 | Bleich |

(Continued)

OTHER PUBLICATIONS

International Search Report and Written Opinion dated Sep. 20, 2019 for International Application No. PCT/US2019/041200.

*Primary Examiner* — Tan-Uyen T Ho
*Assistant Examiner* — Bridget E. Rabaglia
(74) *Attorney, Agent, or Firm* — Seager, Tufte & Wickhem, LLP

(57) ABSTRACT

Medical devices, assemblies and methods for guarding sharp tips of medical needles are disclosed herein. Some embodiments include an expandable device configured to be at least partially disposed within the needle lumen. The device may include an expandable distal portion that is designed to shift between a first configuration in which the expandable distal portion has an outer diameter that is the same as or less than the inner diameter of the needle lumen and a second configuration in which the expandable distal portion has an outer diameter that is greater than the inner diameter of the needle lumen. An elongated inner member may be used to shift the expandable distal portion from the first configuration to the second configuration.

16 Claims, 16 Drawing Sheets

(56) References Cited

U.S. PATENT DOCUMENTS

| | | |
|---|---|---|
| 2011/0046512 A1 | 2/2011 | Bacon et al. |
| 2012/0022399 A1 | 1/2012 | Mumaw |
| 2012/0022400 A1 | 1/2012 | Mumaw |
| 2014/0046320 A1 | 2/2014 | Kappel et al. |
| 2016/0120518 A1* | 5/2016 | Geist .................. A61B 10/0233 600/566 |
| 2016/0157839 A1 | 6/2016 | Eckerline et al. |
| 2016/0178519 A1 | 6/2016 | Zupkofska et al. |
| 2016/0331358 A1 | 11/2016 | Gordon |
| 2017/0245841 A1 | 8/2017 | Fleury et al. |
| 2017/0258521 A1 | 9/2017 | Asirvatham et al. |
| 2018/0043139 A1 | 2/2018 | Haindl |

\* cited by examiner

EXPANDABLE MEDICAL DEVICE FOR USE WITH A NEEDLE

CROSS-REFERENCE TO RELATED APPLICATIONS

This application claims the benefit of priority under 35 U.S.C. § 119 of U.S. Provisional Application No. 62/696,516, filed Jul. 11, 2018, the entire disclosure of which is hereby incorporated by reference.

TECHNICAL FIELD

The present disclosure pertains to medical devices, and methods for manufacturing medical devices. More particularly, the present disclosure pertains to medical needles, and devices and assemblies for guarding sharp tips of medical needles, and methods for manufacturing and using such devices and assemblies.

BACKGROUND

A wide variety of medical devices have been developed for medical use, for example, medical needles having sharp tips, such as biopsy needles. In some situations, it may be desirable to provide a medical device, assembly, or method for guarding and/or protecting the sharp distal tip of a medical needle. Of the known medical devices and methods, each has certain advantages and disadvantages. There is an ongoing need to provide alternative medical devices as well as alternative methods for manufacturing and using such medical devices.

BRIEF SUMMARY

This disclosure provides design, material, manufacturing method, and use alternatives for medical devices, for example, medical needle assemblies, expandable devices for use with medical needles, stylets for use with medical needles, and the like.

An example embodiment includes a medical needle assembly including a needle having a needle body including a sharp distal tip and having a needle lumen defining an inner diameter. The assembly includes an elongated tubular member configured to be at least partially disposed within the needle lumen and including an expandable distal portion having an inner lumen defining an inner surface. The expandable distal portion is designed to shift between a first configuration in which the expandable distal portion has an outer diameter that is the same as or less than the inner diameter of the needle lumen and a second configuration in which the expandable distal portion has an outer diameter that is greater than the inner diameter of the needle lumen. The assembly includes an elongated inner member configured to shift the expandable distal portion from the first configuration to the second configuration.

Alternatively, or additionally to any of the embodiments above or below, wherein expandable distal portion is disposed distal of and adjacent to the sharp distal tip when in the second configuration such that the expandable distal portion guards the sharp distal tip of the needle.

Alternatively, or additionally to any of the embodiments above or below, wherein the elongated inner member defines an outer surface, wherein the outer surface of the elongate inner member engages the inner surface of the expandable distal portion to shift the expandable distal portion from the first configuration to the second configuration.

Alternatively, or additionally to any of the embodiments above or below, wherein the outer surface of the elongate inner member is engaged with the inner surface of the expandable distal portion when the expandable distal portion is in the second configuration.

Alternatively, or additionally to any of the embodiments above or below, wherein the elongated inner member defines an outer surface, wherein the outer surface of the elongate inner member disengages from the inner surface of the expandable distal portion to shift the expandable distal portion from the second configuration to the first configuration.

Alternatively, or additionally to any of the embodiments above or below, wherein the outer surface of the elongate inner member is disengaged from the inner surface of the expandable distal portion when the expandable distal portion is in the first configuration.

Alternatively, or additionally to any of the embodiments above or below, wherein the expandable distal portion has an inner diameter, and the elongated inner member has an outer diameter, and when in the first configuration, the outer diameter of the elongated inner member is greater than the inner diameter of the expandable distal portion.

Alternatively, or additionally to any of the embodiments above or below, wherein the inner member includes a proximal segment and a distal segment, and the distal segment includes the outer diameter that is greater than the inner diameter of the expandable distal portion, and the proximal segment includes an outer diameter that is less than the outer diameter of the distal segment.

Alternatively, or additionally to any of the embodiments above or below, wherein the elongated tubular member includes a proximal body portion having a first wall thickness, and the distal expandable portion has a second wall thickness that is greater than the first wall thickness.

Alternatively, or additionally to any of the embodiments above or below, wherein the elongated tubular member comprises a coil.

Alternatively, or additionally to any of the embodiments above or below, wherein the distal expandable portion comprises a coil.

Alternatively, or additionally to any of the embodiments above or below, wherein the distal expandable portion comprises a tubular body including an expansion relief slot formed therein.

Another example embodiment includes an expandable device for guarding a sharp distal tip of a needle defining a lumen. The expandable device includes an elongated tubular member including a body portion configured to be at least partially disposed within the needle lumen, and an expandable distal portion defining an inner lumen including an inner surface. The expandable distal portion is designed to shift between a first configuration in which the expandable distal portion has an outer diameter that is the same or less than the inner diameter of the needle lumen and a second configuration in which the expandable distal portion has an outer diameter that is greater than the inner diameter of the needle lumen and is configured to guard the sharp distal tip of the needle. The expandable device also includes an elongated inner member configured to be at least partially disposed within the inner lumen of the elongated tubular member and being configured to shift the expandable distal portion between the first configuration and the second configuration.

Alternatively, or additionally to any of the embodiments above or below, wherein when in the second configuration the outer diameter of the expandable distal portion is greater than an outer diameter of the body portion.

Alternatively, or additionally to any of the embodiments above or below, wherein the elongated inner member defines an outer surface, wherein the outer surface of the elongate inner member engages the inner surface of the expandable distal portion to shift the expandable distal portion from the first configuration to the second configuration.

Alternatively, or additionally to any of the embodiments above or below, wherein the outer surface of the elongate inner member is engaged with the inner surface of the expandable distal portion when the expandable distal portion is in the second configuration.

Alternatively, or additionally to any of the embodiments above or below, wherein the elongated inner member defines an outer surface, wherein the outer surface of the elongate inner member disengages from the inner surface of the expandable distal portion to shift the expandable distal portion from the second configuration to the first configuration.

Alternatively, or additionally to any of the embodiments above or below, wherein the outer surface of the elongate inner member is disengaged from the inner surface of the expandable distal portion when the expandable distal portion is in the first configuration.

Alternatively, or additionally to any of the embodiments above or below, wherein the expandable distal portion has an inner diameter, and the elongated inner member has an outer diameter, and when in the first configuration, the outer diameter of the elongated inner member is greater than the inner diameter of the expandable distal portion.

Alternatively, or additionally to any of the embodiments above or below, wherein the inner member includes a proximal segment and a distal segment, and the distal segment includes the outer diameter that is greater than the inner diameter of the expandable distal portion, and the proximal segment includes an outer diameter that is less than the outer diameter of the distal segment.

Alternatively, or additionally to any of the embodiments above or below, wherein the elongated tubular member includes a proximal body portion having a first wall thickness, and the distal expandable portion has a second wall thickness that is greater than the first wall thickness.

Alternatively, or additionally to any of the embodiments above or below, wherein the elongated tubular member comprises a coil.

Alternatively, or additionally to any of the embodiments above or below, wherein the distal expandable portion comprises a coil.

Alternatively, or additionally to any of the embodiments above or below, wherein the distal expandable portion comprises a tubular body including an expansion relief slot formed therein.

An example embodiment includes method of guarding a sharp tip of a needle having a needle lumen. The method includes disposing an elongated tubular member having an expandable distal portion within the needle lumen such that the expandable distal portion is distal of the sharp tip, the expandable distal portion being in a first configuration in which the expandable distal portion has an outer diameter that is the same or less than an inner diameter of the needle lumen. The method further includes shifting the expandable distal portion to a second configuration in which the expandable distal portion has an outer diameter that is greater than the inner diameter of the needle lumen, wherein an elongated inner member is used to shift the expandable distal portion from the first configuration to the second configuration.

Alternatively, or additionally to any of the embodiments above or below, wherein the elongated inner member defines an outer surface and the expandable distal portion has an inner lumen defining an inner surface, wherein shifting the expandable distal portion from the first configuration to the second configuration includes engaging the outer surface of the elongate inner member with the inner surface of the expandable distal portion such that the outer diameter of the expandable distal portion increases.

Alternatively, or additionally to any of the embodiments above or below, further including shifting the expandable distal portion from the second configuration to the first configuration by disengaging the outer surface of the elongate inner member from the inner surface of the expandable distal portion such that the outer diameter of the expandable distal portion decreases.

Alternatively, or additionally to any of the embodiments above or below, wherein the elongated inner member is used to shift the expandable distal portion from the first configuration to the second configuration by moving the elongated inner member longitudinally into the inner lumen of expandable distal portion.

Alternatively, or additionally to any of the embodiments above or below, wherein the elongated inner member is used to shift the expandable distal portion from the second configuration to the first configuration by moving the elongated inner member longitudinally out of the inner lumen of expandable distal portion.

Alternatively, or additionally to any of the embodiments above or below, wherein the expandable distal portion has an inner diameter, and the elongated inner member has an outer diameter, and when in the first configuration, the outer diameter of the elongated inner member is greater than the inner diameter of the expandable distal portion.

Alternatively, or additionally to any of the embodiments above or below, wherein the inner member includes a proximal segment and a distal segment, and the distal segment includes the outer diameter that is greater than the inner diameter of the expandable distal portion, and the proximal segment includes an outer diameter that is less than the outer diameter of the distal segment.

Alternatively, or additionally to any of the embodiments above or below, wherein the elongated tubular member includes a proximal body portion having a first wall thickness, and the distal expandable portion has a second wall thickness that is greater than the first wall thickness.

Alternatively, or additionally to any of the embodiments above or below, wherein the elongated tubular member comprises a coil.

Alternatively, or additionally to any of the embodiments above or below, wherein the distal expandable portion comprises a coil.

Alternatively, or additionally to any of the embodiments above or below, wherein the distal expandable portion comprises a tubular body including an expansion relief slot formed therein.

Another example embodiment includes a medical needle assembly including a needle having a needle body including a sharp distal tip and having a needle lumen. The assembly includes an elongated stylet including a proximal segment, a distal segment, and an intermediate segment, wherein the distal segment includes an elongated tapering stiffness profile, and the intermediate segment is stiffer than the distal segment. The stylet is disposed within the needle lumen such that the rigid intermediate segment is within the sharp distal tip, and the tapered distal segment extends distally beyond the sharp distal tip.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
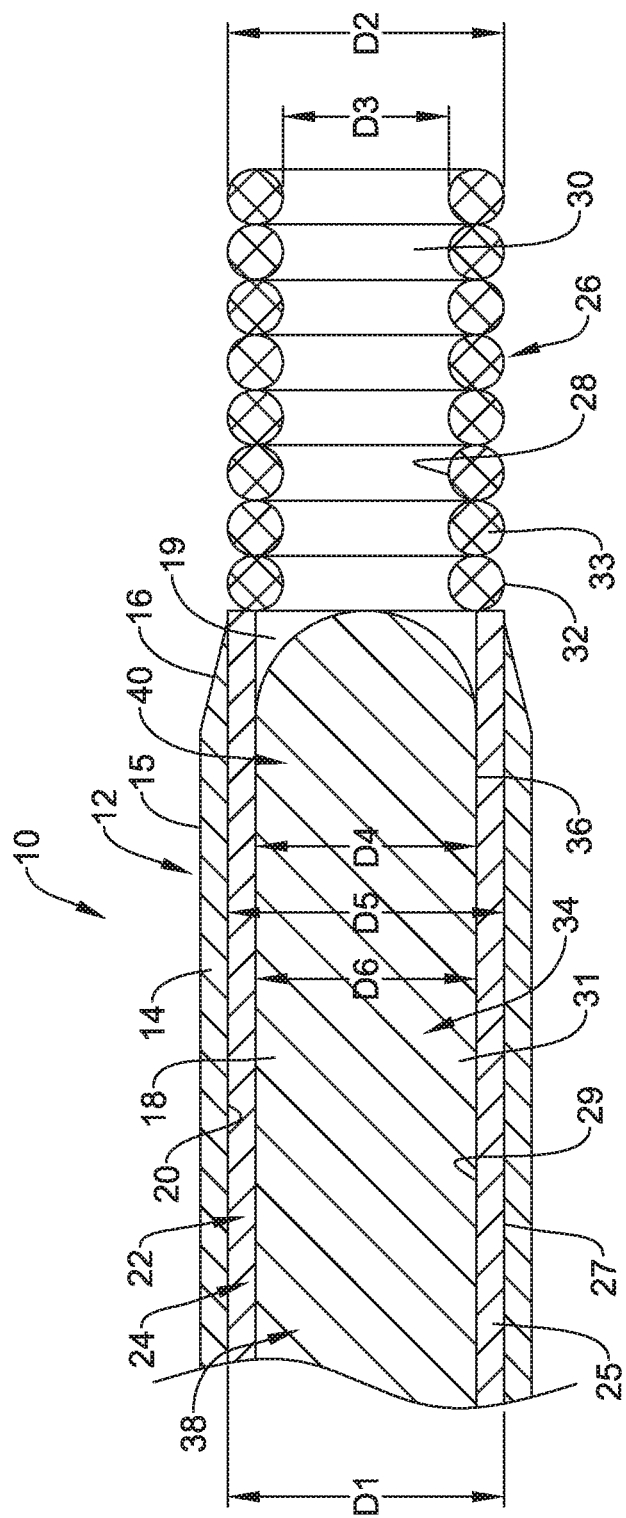
FIG. 1 is a partial cross-sectional side view of an example embodiment of a medical needle assembly including a needle having a sharp distal tip, an elongated tubular member at least partially disposed within the needle lumen and including an expandable distal portion in a first or non-expanded configuration, and an elongate inner member disposed within the elongated tubular member.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Medical needles, such as biopsy, aspiration or delivery needles, are widely utilized throughout the world in medical procedures. Prior to or during use or during delivery, it may be desirable to guard and/or protect the sharp distal tip of a medical needle. For example, needles, such as biopsy needles, may be navigated to a target or treatment site through a delivery device and/or through the anatomy of a patient. It may be desirable to guard or protect the sharp needle tip during such navigation such that the tip does not undesirably skive, scrape, puncture or become embedded or stuck in the delivery device or in the anatomy. Once at the desired site, it may also be desirable to expose or "unguard" the sharp tip of the needle so that it may be used, for example, to take a biopsy sample or aspirate and/or deliver a fluid or material. As such, some embodiments of the present disclosure may include methods and devices that may be configured and used to selectively guard or protect a sharp needle tip when desired and may also be configured and used to selectively allow for exposure of the sharp needle tip for use as desired.

FIG. 1 shows a partial cross-sectional side view of one example embodiment of a medical needle assembly 10. The medical needle assembly 10 includes a needle 12 having a needle body 14 defining a sharp distal tip 16. The needle body 14 has an outer surface 15 and an inner surface 20 and defines a needle lumen 18 having an inner diameter D1. The sharp distal tip 16 defines a distal needle opening 19 into the needle lumen 18. The needle 12 may be of any of a wide variety of medical needles, for example: a biopsy needle; an aspiration needle, such as a needle that may be used for fine needle aspiration; a delivery needle, such as a needle used for the delivery of therapeutic fluid and/or materials; or the like. In the particular embodiment shown, the needle 12 may be a biopsy needle. The sharp distal tip 16 and/or needle opening 19 may be configured to puncture and acquire a sample from tissue. Some example configurations for the sharp distal tip 16 include francine, lancet, beveled, and/or hubers tip configurations, or any other desired needle tip configuration that may be used, for example, in a biopsy and/or aspiration needle, or other type of medical needle. The needle 12 may include or be made of one or more metals, polymers, and/or composite or layered structures thereof, including any of those disclosed herein.

The medical needle assembly 10 also includes an expandable medical device for use with the needle 12. The expandable medical device may be designed to have a first or non-expanded configuration, in which the medical device is configured to selectively allow movement of the needle 12 thereover, for example, to allow exposure of the sharp distal tip 16 when desired. The expandable medical device may be designed to have a second or expanded configuration, in which an expandable portion of the medical device is designed to guard and/or protect the sharp distal tip 16 when so desired. This embodiment includes an elongated tubular member 22 configured to be at least partially disposed within the needle lumen 18. The elongated tubular member 22 includes a proximal body portion 24 and an expandable distal portion 26, which is configured to shift between a first, radially non-expanded configuration and a second, radially expanded configuration, for example, through the use of an elongated inner member 34.

The proximal body portion 24 has an outer surface 27 and an inner surface 29, which defines an inner lumen 31. The proximal body portion 24 has a wall 25 having a first wall thickness which is defined between the outer surface 27 and the inner surface 29. The proximal body portion 24 may have an outer diameter D5. The outer diameter D5 may be sized and/or configured such that the proximal body portion 24 may fit within, and/or be longitudinally movable within, the needle lumen 18. For example, the proximal body portion 24 may have an outer diameter D5 that is less than the inner diameter D1 of the needle lumen 18, such that the proximal body portion 24 may be disposed within the needle lumen 18. The proximal body portion 24 may have an inner diameter D4, defined by the inner lumen 31, which may be configured to accept another device therein, such as the elongated inner member 34, as discussed in more detail below and herein. The proximal body portion 24 may include any structure as desired, such as a solid tubular member, extrusion, coil, braid, mesh, or the like. In the embodiment shown, the proximal body portion 24 comprises a solid tubular member. The proximal body portion 24 may include or be made of one or more metals, polymers, and/or composite or layered structures thereof, including any of those disclosed herein.

The expandable distal portion 26 has an inner surface 28 defining an inner lumen 30, and an outer surface 32. The inner lumen 30 may be connected to and/or in fluid communication with the inner lumen 31 of the body portion 24. The inner lumens 30 and 31 may be coaxial with one another and may be configured such that a device (such as the elongate inner member 34) may extend and/or be moved longitudinally from one lumen (e.g. lumen 31) into the other lumen (e.g. lumen 30) when so desired. The expandable distal portion 26 has a wall 33 having a second wall thickness that is defined between the inner surface 28 and the outer surface 32. In the embodiment shown, the second wall thickness (the wall thickness of the expandable distal portion 26) is greater than the first wall thickness (the wall thickness of the proximal body portion 24). The expandable distal portion 26 may have an outer diameter D2 and an inner diameter D3. The expandable distal portion 26 may be configured to radially expand and/or contract such that it can shift between a first, radially non-expanded configuration and a second, radially expanded configuration, as will be discussed in more detail below and herein. The expandable distal portion 26 may include any structure as desired, such as a tubular member, extrusion, coil, braid, mesh, or the like. In the embodiment shown, the expandable distal portion 26 comprises a coil member. The expandable distal portion 26 may include or be made of one or more metals, polymers, and/or composite or layered structures thereof, including any of those disclosed herein.

In the particular embodiment shown, the proximal body portion 24 and the expandable distal portion 26 are separate members that are connected together, for example via a bond, such as a weld, solder, braze, adhesive bond, mechanical bond or interlock, or the like, to create the elongated tubular member 22. In other embodiments, however, the body portion 24 and the expandable distal portion 26 may be a single member and/or of unitary and/or monolithic construction. For example, elongated tubular member 22, including the body portion 24 and the expandable distal portion 26, may be a full length singular and/or monolithic structure, such as a tubular member, extrusion, coil, braid, mesh, or the like.

The elongated inner member 34 includes a proximal segment 38 and a distal segment 40 and has an outer surface

36 and an outer diameter D6. The outer diameter D6 may be sized and/or configured such that the elongated inner member 34 may fit within, and/or be longitudinally movable within, the inner lumen 31 of the proximal body portion 24. For example, the elongated inner member 34 may have an outer diameter D6 that is less than the inner diameter D4 of the proximal body portion 24, such that the elongated inner member 34 may be disposed within and/or longitudinally movable within the inner lumen 31. In this embodiment, the proximal segment 38 and the distal segment 40 include the same outer diameter D6. However, in other embodiments, the outer diameter of the elongated inner member 34 may vary along its length between the proximal and distal segments, for example, as will be seen in other embodiments herein. The elongated inner member 34 may be configured and/or arranged to shift the expandable distal portion 26 between the first, or radially non-expanded configuration and the second, or radially expanded configuration. For example, the elongated inner member 34 may include an outer diameter D6 that is larger than the inner diameter D3 of the expandable distal portion 26 when in the first, or radially non-expanded configuration. The elongated inner member 34 may be a solid or tubular structural member, and may take the form of such devices as a core member, a guidewire, a dilator, a trocar, an obturator, or the like, or any other such structural member or device.

As indicated herein, the expandable distal portion 26 is designed to shift between a first, radially non-expanded configuration, and a second, radially expanded configuration. FIG. 1 shows the expandable distal portion 26 in the first configuration, in which the expandable distal portion 26 has an outer diameter D2 that is the same as or less than the inner diameter D1 of the needle lumen 18. In this configuration, the elongated inner member 34, including the outer diameter D6, is disposed within the inner lumen 31 of the proximal body portion 24, and is disposed proximal of the distal expandable portion 26. As such, the outer surface 36 of the elongated inner member 34 is not engaged with and/or is disengaged from the inner surface 28 of the expandable distal portion 26. The expandable distal portion 26 in this first configuration may have an outer diameter D2 that is configured to fit within, and/or be longitudinally movable within, the needle lumen 18. As such, in this first configuration, the needle 12, including the sharp distal tip 16, may be longitudinally moved over and/or about the expandable distal portion 26, and/or the expandable distal portion 26 may be moved within the needle 12 such that it is disposed within and/or movable within the needle lumen 18. In this first configuration, the sharp needle tip may be considered to not be radially protected and/or guarded by the expandable distal portion 26, relative to when in the second expanded configuration.

In this embodiment, when in the first configuration, the inner diameter D3 of the expandable distal portion 26 may be less than the inner dimeter D4 of the proximal body portion 24. Additionally, the outer diameter D2 of the expandable distal portion 26 may be the same as the outer diameter D5 of the proximal body portion 24. As can be appreciated, the variance in the wall thickness between the distal expandable portion 26 and the body portion 24 may allow this to be achieved. However, other embodiments may have different configurations. For example, it is contemplated that in some embodiments, when in the first configuration, the outer diameter D2 of the expandable distal portion 26 may be less than the outer diameter D5 of the proximal body portion 24, as long as the expandable distal portion 26 has enough wall thickness to allow for adequate radial expansion of the outer diameter D2 when shifted to the second configuration (as discussed in more detail below).

Figure 2:
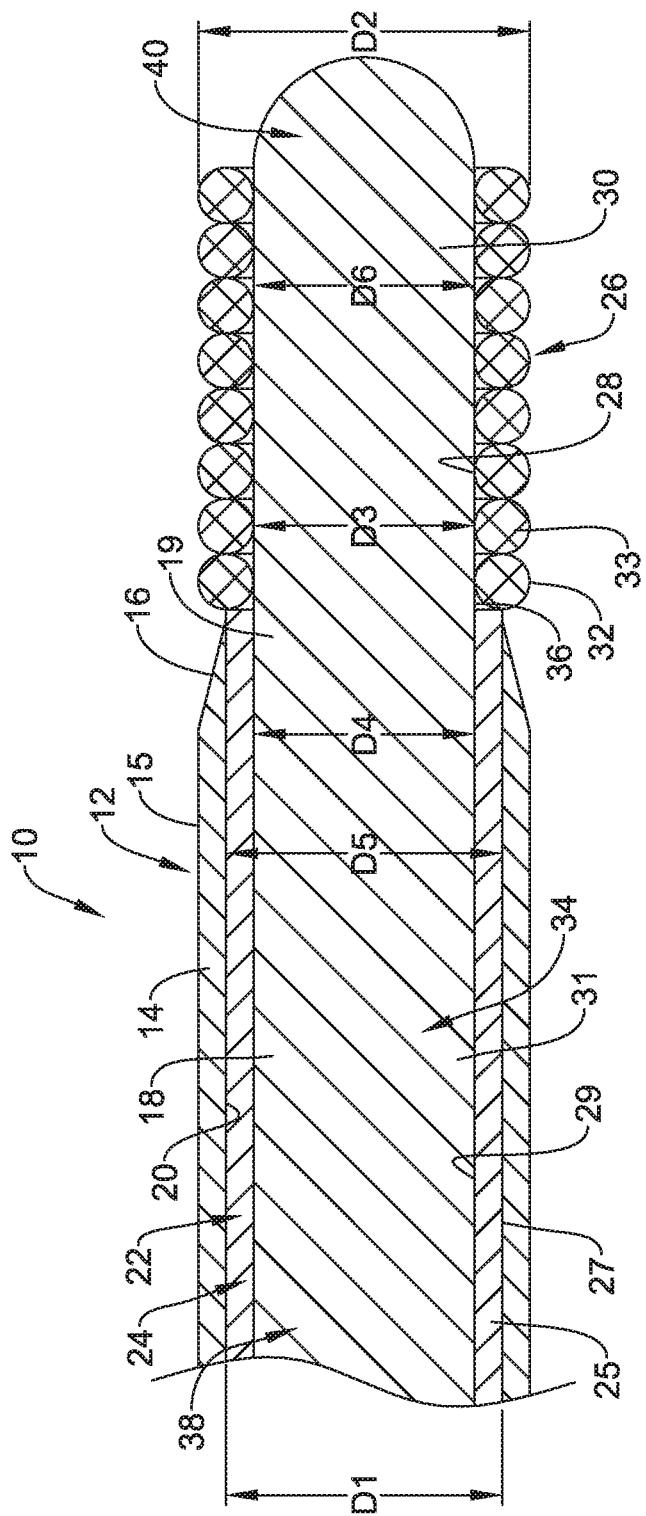
FIG. 2 is a partial cross-sectional side view of the example embodiment of FIG. 1, with the expandable distal portion shown in a second or expanded configuration guarding the sharp distal tip of the needle.

FIG. 2 shows the expandable distal portion 26 in the second configuration, in which the expandable distal portion 26 has an outer diameter D2 that is larger than the inner diameter D1 of the needle lumen 18. The elongated inner member 34 has been moved longitudinally in a distal direction and forced into the inner lumen 30 of the expandable distal portion 26 with a predetermined amount of force, such that the outer surface 36 of the elongated inner member 34 engages and/or is engaged with the inner surface 28 of the expandable distal portion 26. Because the outer diameter D6 of the elongated inner member 34 is larger than the initial (e.g. non-expanded) inner diameter D3 of the expandable distal member 26, as the elongated inner member 34 is inserted therein, it forces the expandable distal member 26 to expand radially. This radial expansion thus increased both the inner diameter D3 and outer diameter D2 of the expandable distal member 26 when in the second configuration relative to these diameters in the first configuration. As such, when in the second configuration, the inner diameter D3 of the expandable distal member 26 is about the same (or slightly less than) as the outer diameter D6 of the elongated inner member 34, and the outer diameter D2 is larger than the inner diameter D1 of the needle lumen 18. As such, the expandable distal portion 26 when in this second configuration may have an outer diameter D2 that is configured such that it cannot fit within and/or be longitudinally movable within, the needle lumen 18. The expandable distal portion 26 is disposed adjacent to the sharp distal tip 16, and now has a larger diameter D2, and thus may act to guard and/or protect the sharp distal tip 16. As such, in this configuration, the sharp distal tip 16 may be considered to be radially protected and/or guarded by the expandable distal portion 26.

In this embodiment, when in the second configuration, the outer diameter D2 of the expandable distal portion 26 may be larger than the outer diameter D5 of the proximal body portion 24. Additionally, when in the second configuration, the inner diameter D3 of the expandable distal portion 26 may be the same as the inner dimeter D4 of the proximal body portion 24. As can be appreciated, the variance in the wall thickness between the distal expandable portion 26 and the body portion 24 may allow this to be achieved. However, other embodiments may have different configurations. For example, it is contemplated that in some embodiments, when in the second configuration, the inner diameter D3 of the expandable distal portion 26 may be less than the inner dimeter D4 of the proximal body portion 24, as long as the expandable distal portion 26 has enough wall thickness to allow for adequate radial expansion for the outer diameter D2 to be larger than the inner diameter D1 of the needle lumen 18 when in the second configuration.

The expandable medical device as disclosed herein can thus be used in a method of guarding the sharp tip of the needle 12. The elongated tubular member 22 having the expandable distal portion 26 in the first configuration can be disposed within the needle lumen 18 such that the expandable distal portion 26 is distal of the sharp distal tip 16, as shown in FIG. 1. The expandable distal portion 26 can then be shifted to the to the second configuration, as shown in FIG. 2, using the elongated inner member 34 to shift the expandable distal portion 26 from the first configuration to the second configuration.

The expandable distal portion 26 may be configured to be biased toward the first and/or unexpanded configuration. For example, when relaxed (e.g. without the application of the predetermined shifting force), the expandable distal portion 26 may be configured to be in the unexpanded configuration, for example as shown in FIG. 1. The expandable distal portion 26 may include structure and/or be made of a material that may help achieve this. For example, expandable distal portion 26 may include structure and/or may be made of a resilient and/or elastic material that may allow for the expandable distal portion 26 to be mechanically and/or elastically biased to the first or unexpanded configuration. The expandable distal portion 26 may be shifted from the first configuration to the second configuration though the application of the predetermined shifting force (e.g. applied through the elongated inner member 34), and then may mechanically and/or elastically reverted back and/or recover to the first configuration once the predetermined shifting force is removed (e.g. the elongated inner member 34 is removed from therein). The expandable distal portion 26 may include and/or be made of a tube, such as a slotted or cut tube, a winding, a braid, a coil, a mesh, or the like, which may be structurally configured to allow such elastic expansion and/or contraction. In the embodiment shown in FIGS. 1 and 2, the expandable distal portion 26 includes a coiled member that may include a spring force that may allow for radial expansion and contraction as desired.

In that regard, the expandable distal portion 26 may be shifted from the second, expanded configuration as shown in FIG. 2, to the first, unexpanded configuration, as shown in FIG. 1, by removing the predetermined expansion force applied by the elongated inner member 34. For example, by moving the elongated inner member 34 longitudinally in a proximal direction out of the inner lumen 30 of the expandable distal portion 26, the outer surface 36 of the elongated inner member 34 will disengage from the inner surface 28 of the expandable distal portion 26. As such, the expandable distal portion 26 may revert and/or relax back to the first configuration, wherein the expandable distal portion 26 has an outer diameter D2 that is the same as or less than the inner diameter D1 of the needle lumen 18, as shown in FIG. 1.

As indicated herein, it may be desirable to guard and/or protect the sharp distal tip 16 of the needle 12 as the needle 12 is navigated to a target or treatment site through a delivery device and/or through the anatomy of a patient, such that the tip does not undesirably skive, scrape, puncture or become embedded or stuck in the delivery device or in the anatomy. It is then also desirable to expose or "unguard" the sharp distal tip 16 of the needle 12 for use at the target or treatment site. An example method of using the medical needle assembly 10 described above with reference to FIGS. 1 and 2 will now be shown and described with reference to FIGS. 3-7.

Figure 3:
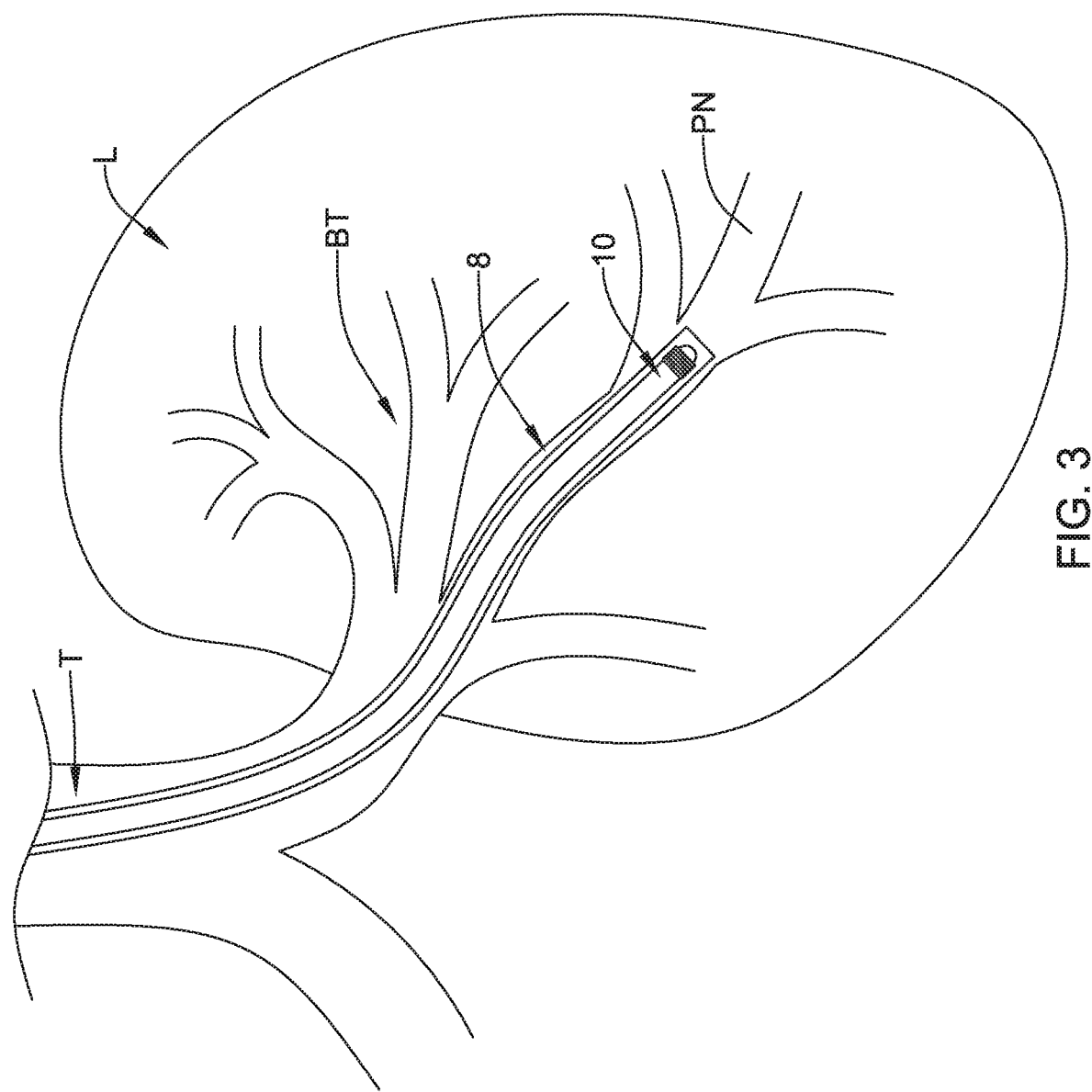
FIG. 3 is a partial cross-sectional plan view showing a delivery device advanced within the anatomy of a patient, and the example medical needle assembly of FIG. 2 shown being advanced through the delivery device with the expandable distal portion in the second or expanded configuration, guarding the sharp distal tip of the needle during delivery.

FIG. 3 is a partial cross-sectional plan view showing a delivery device 8 advanced within the anatomy of a patient. In this example, the delivery device 8 is advanced through the trachea T and the bronchial tree BT to a location adjacent a peripheral node PN in the lung L of a patient. The medical needle assembly 10 is shown advanced through the delivery device 8, and may be used to take a biopsy sample of the peripheral node. The delivery device 8 can be any suitable device configured for delivery of the needle assembly 10. Some examples of suitable delivery devices may include an endoscope, a delivery sheath, a guide catheter, a delivery tube, or the like. In yet other embodiments, a delivery device may not be necessary, and the needle assembly 10 may be delivered and/or navigated directly though the anatomy of the patient.

Figure 4:
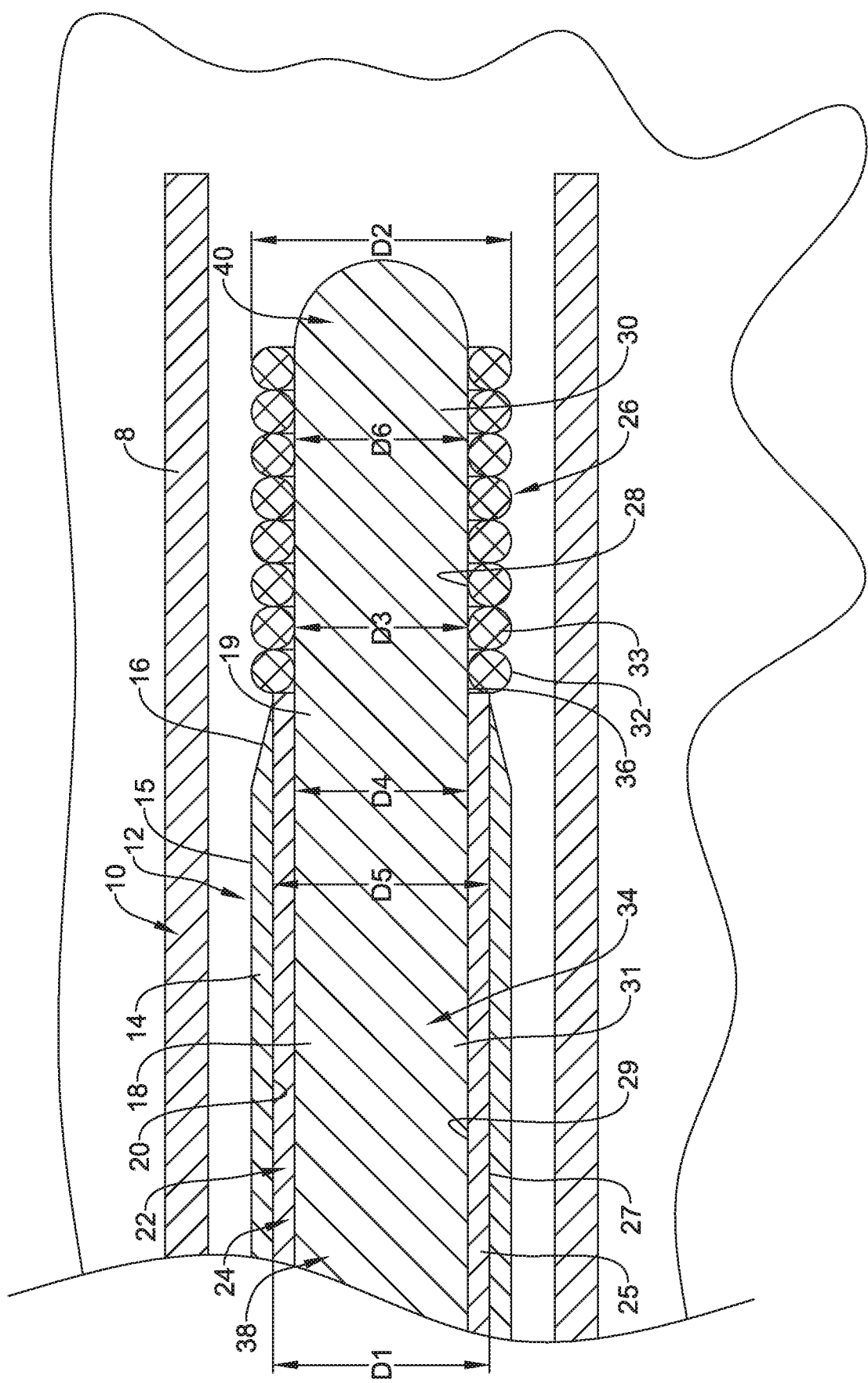
FIG. 4 is a close-up cross-sectional side view of the distal portion of the delivery device and the medical needle assembly of FIG. 3, with the expandable distal portion in the second or expanded configuration.

FIG. 4 is a close-up cross-sectional side view of the distal portion of the delivery device 8 and the medical needle assembly 10 being advanced therein. As can be appreciated, the expandable distal portion 26 is in the second, expanded configuration as shown and described above with reference to FIG. 2, in which the expandable distal portion 26 has an outer diameter D2 that is larger than the inner diameter D1 of the needle lumen 18. In this configuration the sharp distal tip 16 may be considered to be radially protected and/or guarded by the expandable distal portion 26. This may aid in navigating to a target or treatment site through a delivery device 8 such that the sharp distal tip 16 does not undesirably skive, scrape, puncture or become embedded or stuck in the delivery device 8.

Figure 5:
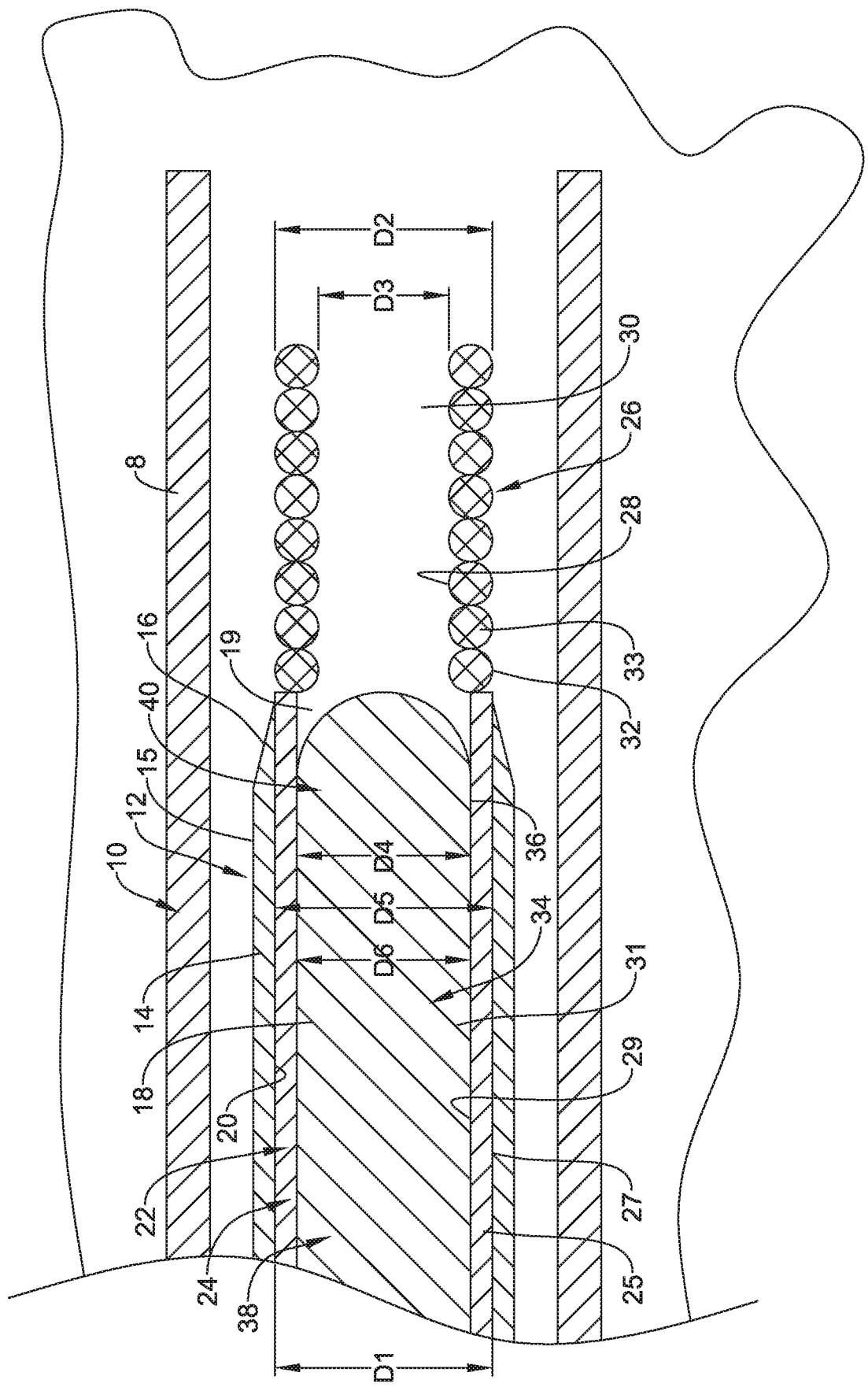
FIG. 5 is a partial cross-sectional side view of the delivery device and the medical needle assembly of FIG. 4, showing the expandable distal portion shifted to the first or non-expanded configuration.

As shown in FIG. 5, once the medical needle assembly 10 is navigated as desired to close proximity to a target and/or treatment cite, the expandable distal portion 26 may be shifted from the second, expanded configuration to the first, non-expanded configuration, as shown and described above with reference to FIGS. 1 and 2. As described above, in the first configuration, the expandable distal portion 26 has an outer diameter D2 that is the same as or less than the inner diameter D1 of the needle lumen 18. In this first configuration, the sharp distal tip 16 may be considered to not be radially protected and/or guarded by the expandable distal portion 26, relative to when in the second expanded configuration. Additionally, in this first configuration, the needle 12, including the sharp distal tip 16, may be longitudinally moved over and/or about and/or distally beyond the expandable distal portion 26.

Figure 6:
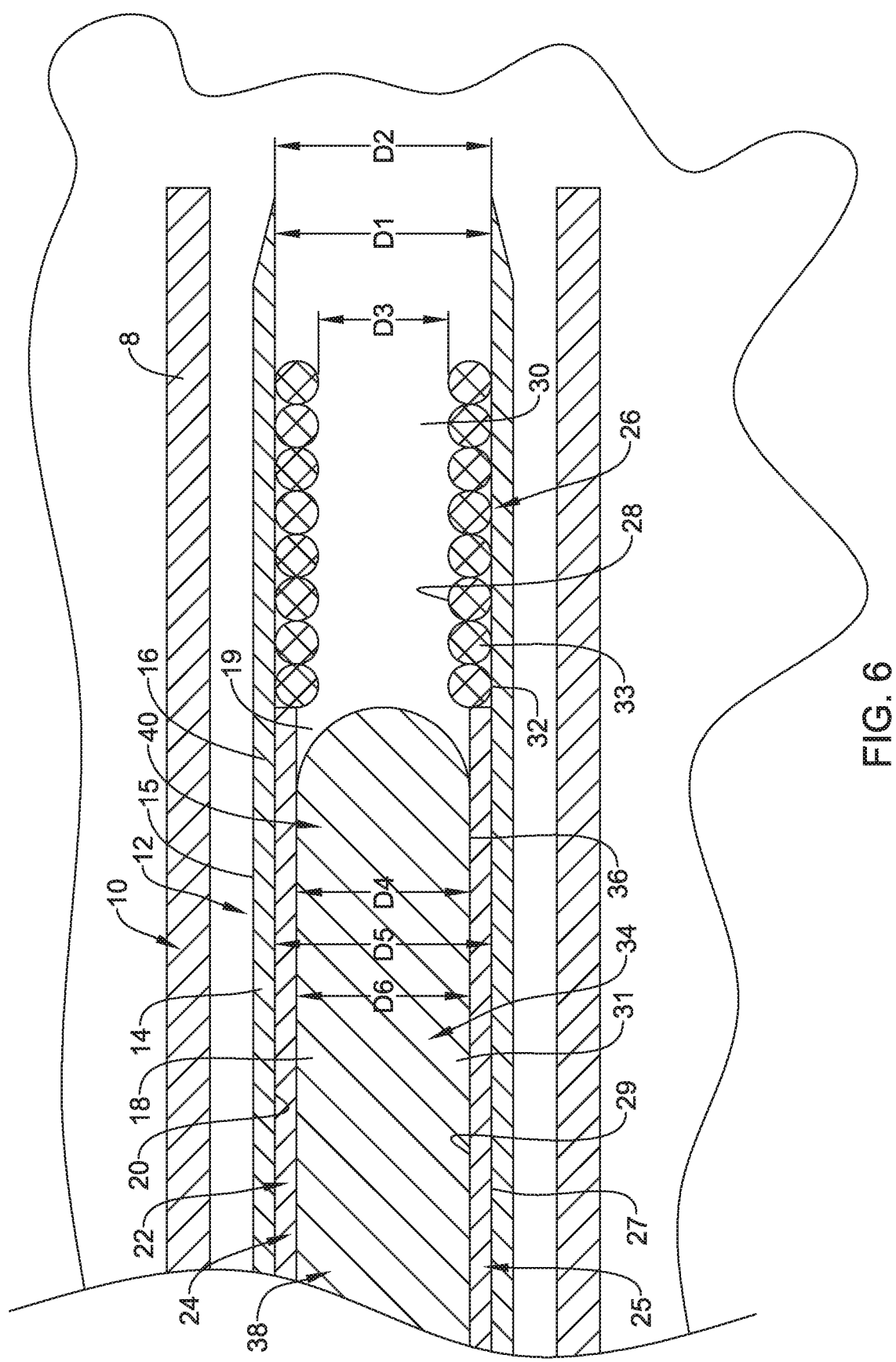
FIG. 6 is a partial cross-sectional side view of the delivery device and the medical needle assembly of FIG. 5, showing the expandable distal portion in the first or non-expanded configuration, and the needle being advanced distally over the expandable distal portion.

For example, FIG. 6 shows the needle 12 being advanced distally over the expandable distal portion 26 (which is in the first, non-expanded configuration) such that the sharp distal tip 16 is distal of the expandable distal portion 26 and is exposed for use, for example, in taking a biopsy sample.

Figure 7:
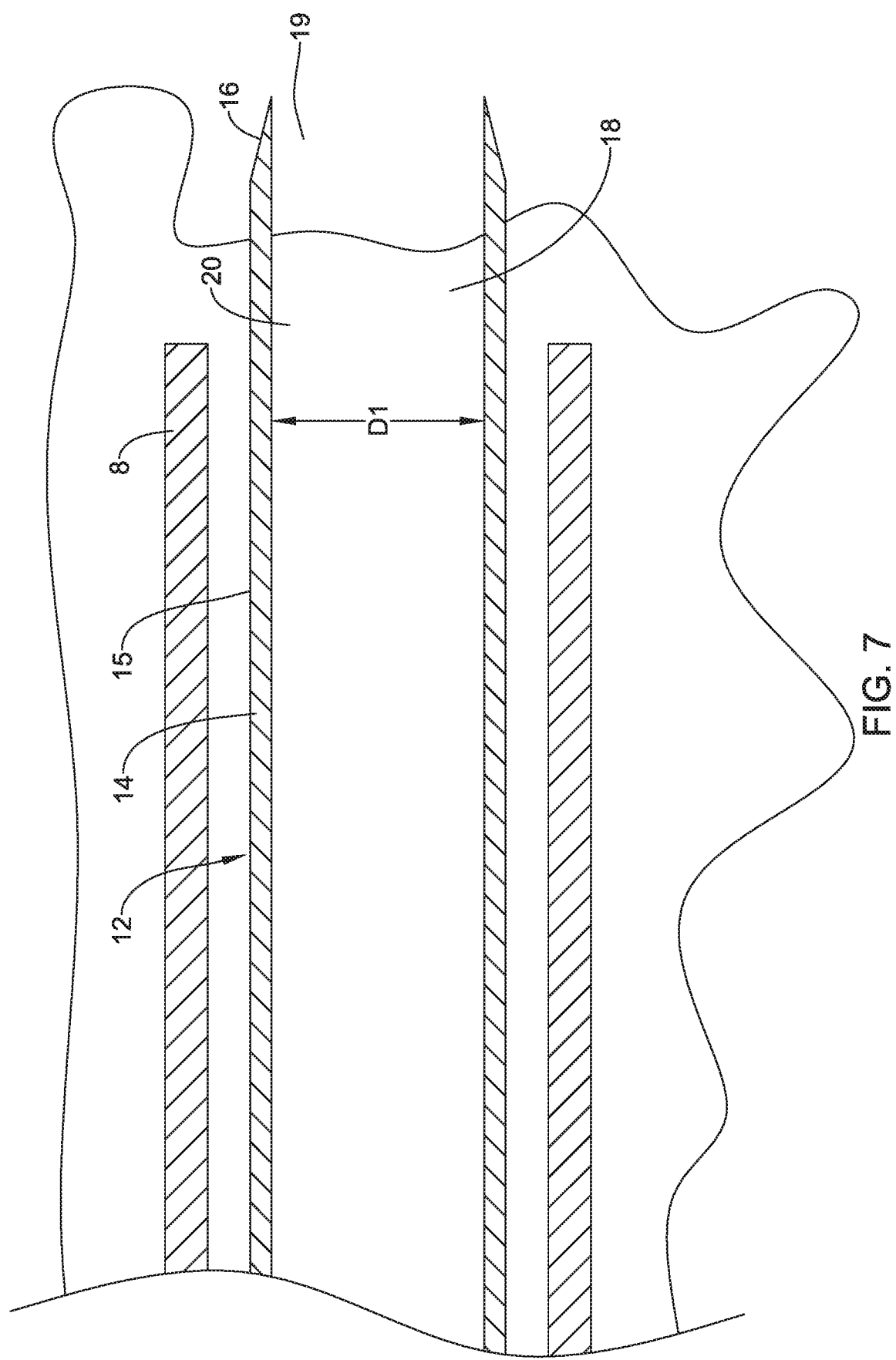
FIG. 7 is a partial cross-sectional side view of the delivery device and the medical needle of FIG. 6, wherein the elongated tubular member, including an expandable distal portion, and an elongate inner member have been removed from the distal portion of the needle, and the needle is being advanced into tissue to obtain a sample.

FIG. 7 then shows the sharp distal tip 16 being advanced into tissue to obtain a biopsy sample. In FIG. 7, the entire expandable medical device, including the elongated tubular member 22 (which includes the proximal body portion 24 and the expandable distal portion 26) and the elongated inner member 34, have been removed from the needle 12, for example, by withdrawing them proximally through the needle 12. After the needle 12 has been used to obtain a biopsy sample, the needle 12 (including the tissue sample) and delivery device 8 may be removed from the anatomy.

FIGS. 8-15 show some additional example embodiments of needle assemblies and/or expandable medical devices in accordance with this disclosure that may be the same or similar in form and function to the needle assembly 10 and/or the expandable medical device described above. These example needle assemblies and/or expandable medical devices each include an elongated tubular member configured to be at least partially disposed within the needle lumen. Each of the elongated tubular members include a proximal body portion and an expandable distal portion, which is configured to shift between a first, radially non-expanded configuration and a second, radially expanded configuration, for example, through the use of an elongated inner member. The structures shown, named and numbered similarly in these embodiments may include structure, materials, and/or usage that are the same as or similar to those of any such similarly named and numbered structures shown and described herein, for example, in the embodiment above. Features, structures, materials, and usage of the various embodiments may be combined and/or used in other embodiments. For example, the discussion of the structure, materials, usage, form and/or function of the needle assembly and/or the expandable medical device and/or needle, and/or elongated tubular member and/or expandable distal portion and/or proximal body portion and/or elongated inner member and/or any of the features, parts or components thereof and any related structures in the embodiment above with reference to FIGS. 1-7 may apply equally to any and all of the other embodiments described herein, and vice versa. In particular, the expandable distal portion and the elongated inner member in each of these embodiments, while possibly including some structural differences as noted, may still allow for shifting between a first, radially non-expanded configuration and a second, radially expanded configuration, and may be used for protecting the sharp distal tip of a needle in a similar manner and in accordance with the methods as described herein.

Figure 8:
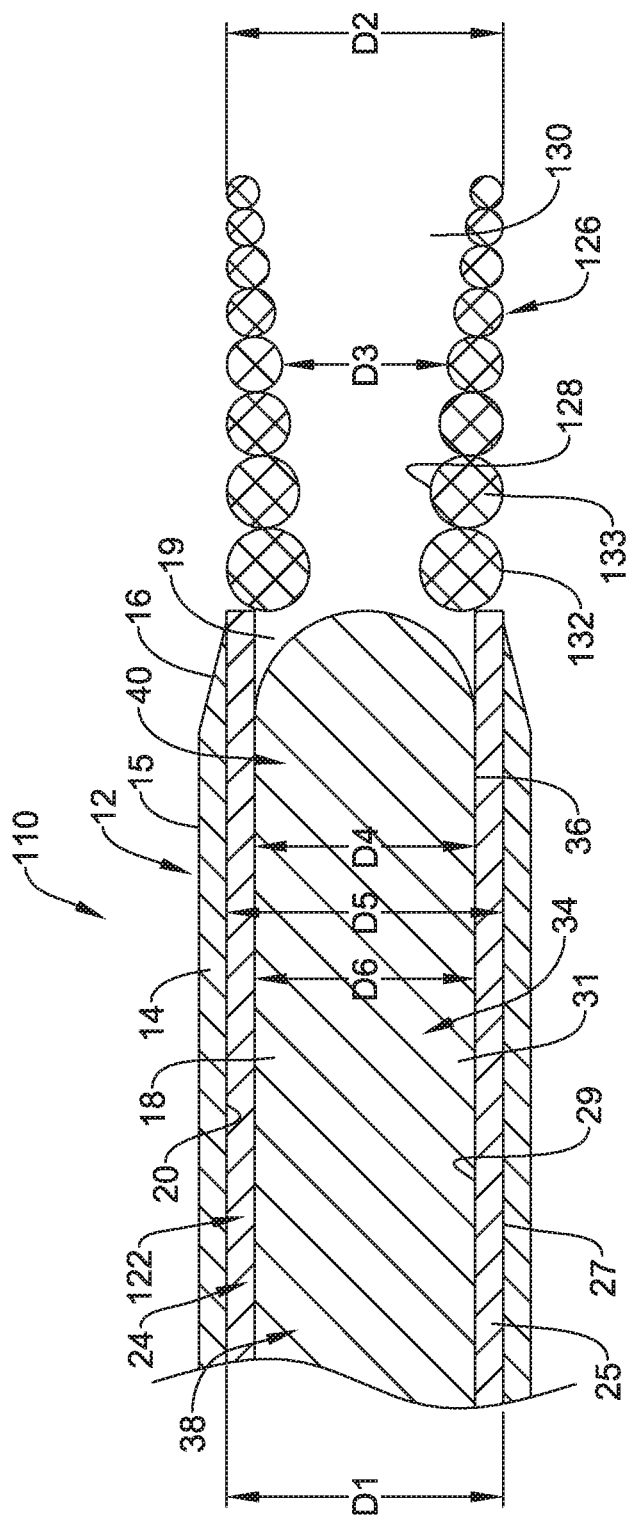
FIG. 8 is a partial cross-sectional side view of another example embodiment of a medical needle assembly including an alternative configuration for the expandable distal portion, which is shown in a first or non-expanded configuration.

FIG. 8 shows a partial cross-sectional view of another example embodiment of a needle assembly 110 similar in form and function to needle assembly 10 shown and described with reference to FIGS. 1 and 2, wherein similarly named structures and/or similarly numbered structures may be similar in form and function as those discussed elsewhere herein. In this embodiment, however, elongated tubular member 122 includes an expandable distal portion 126 that may vary in wall thickness along at least a portion of its length. In the particular embodiment shown, the expandable distal portion 126 includes a tapered coil structure, wherein the diameter of the coil windings decreases as the windings extend distally. However, other embodiments may not include a coil, but some other tubular structure that may be tapered distally. Such a configuration may provide the expandable distal portion 126 with a tapered stiffness profile as it extends distally, with the more proximal portion including the larger wall thickness being stiffer, and the more distal portion including the smaller wall thickness being less stiff.

The expandable distal portion 126 has an inner surface 128 defining an inner lumen 130, and an outer surface 132. The expandable distal portion 126 has a wall 133 having a wall thickness that is defined between the inner surface 128 and the outer surface 132. As may be appreciated, due to the tapered structure, the wall thickness may vary and/or taper along the length of the expandable distal portion 126, with the wall thickness being greatest near the proximal end, and the least near the distal end. The expandable distal portion 126 may have an outer diameter D2 and an inner diameter D3. Similar to and/or because of the wall thickness taper, the inner diameter D3, the outer dimeter D2, or both, may also taper along the length expandable distal portion 126.

Similar to the other embodiments described herein, the expandable distal portion 126 is designed to shift between a first, radially non-expanded configuration, and a second, radially expanded configuration. FIG. 8 shows the expandable distal portion 126 in the first configuration, in which the expandable distal portion 126 has an outer diameter D2 that is the same as or less than the inner diameter D1 of the needle lumen 18. As such, in this first configuration, the needle 12, including the sharp distal tip 16, may be longitudinally moved over and/or about the expandable distal portion 126, and/or the expandable distal portion 26 may be moved within the needle 12 such that it is disposed within and/or movable within the needle lumen 18. In this first configuration, the sharp needle tip 16 may be considered to not be radially protected and/or guarded by the expandable distal portion 126, relative to when in the second expanded configuration.

Figure 9:
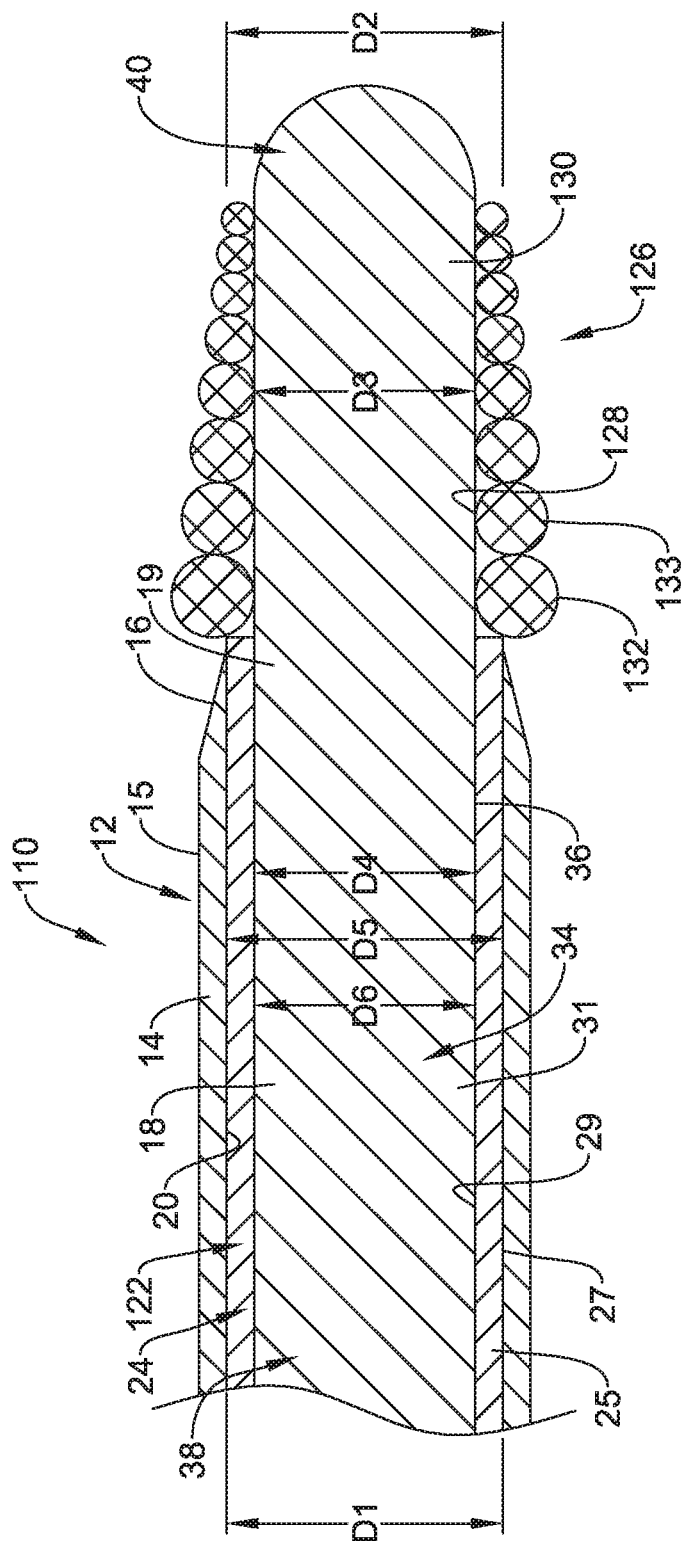
FIG. 9 is a partial cross-sectional side view of the example embodiment of FIG. 8, with the expandable distal portion shown in a second or expanded configuration, guarding the sharp distal tip of the needle.

FIG. 9 shows the expandable distal portion 126 in the second configuration, in which the expandable distal portion 126 has an outer diameter D2 that is larger than the inner diameter D1 of the needle lumen 18. At least a portion, such as the proximal portion, of the expandable distal portion 126 has an outer diameter D2 that is larger than the inner diameter D1 of the needle lumen 18. The elongated inner member 34 has been moved longitudinally in a distal direction and forced into the inner lumen 130 of the expandable distal portion 126 with a predetermined amount of force, such that the outer surface 36 of the elongated inner member 34 engages and/or is engaged with the inner surface 128 of the expandable distal portion 126. Because the outer diameter D6 of the elongated inner member 34 is larger than the initial (e.g. non-expanded) inner diameter D3 of the expandable distal member 126, as the elongated inner member 34 is inserted therein, it forces the expandable distal member 126 to expand radially. This radial expansion thus increases both the inner diameter D3 and outer diameter D2 of the expandable distal portion 126 when in the second configuration relative to these diameters in the first configuration. As such, the expandable distal portion 126 when in this second configuration may have an outer diameter D2 that is configured such that it cannot fit within and/or be longitudinally movable within the needle lumen 18. The expandable distal portion 126 is disposed adjacent to the sharp distal tip 16, and now has a larger diameter D2, and thus may act to guard and/or protect the sharp distal tip 16. As such, in this configuration, the sharp distal tip 16 may be considered to be radially protected and/or guarded by the expandable distal portion 126.

Figure 10:
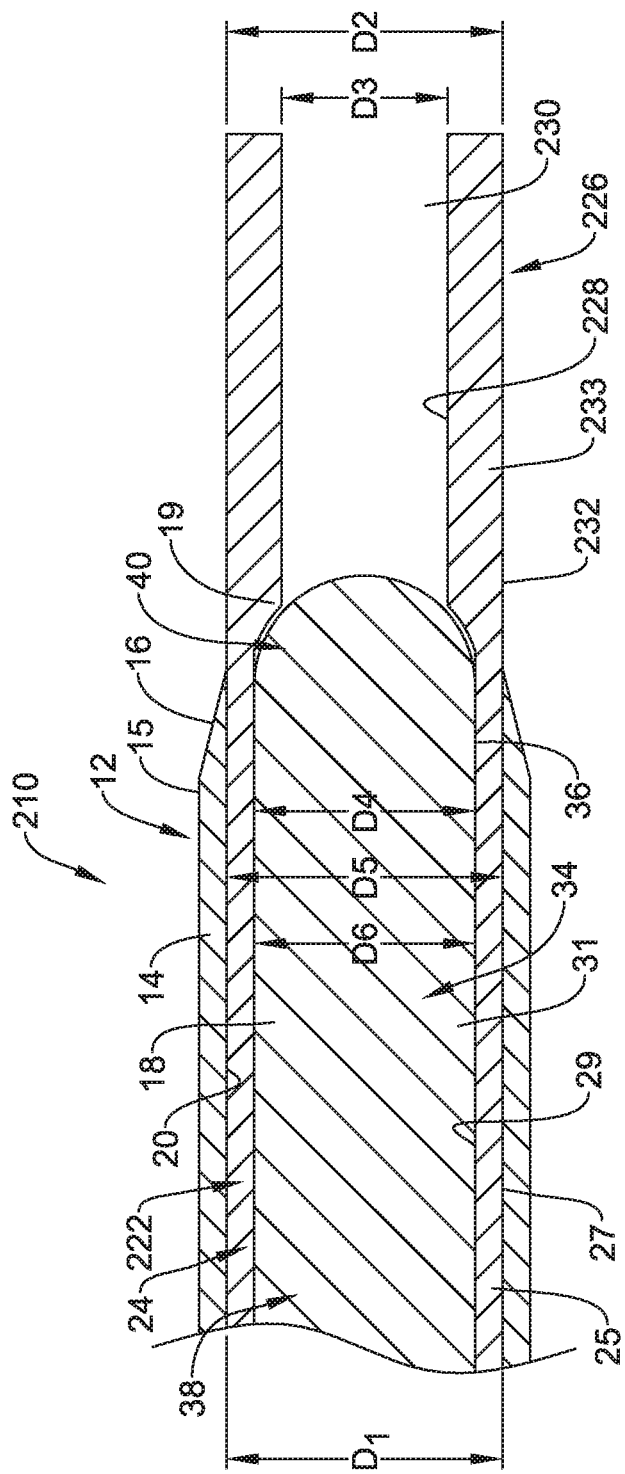
FIG. 10 is a partial cross-sectional side view of another example embodiment of a medical needle assembly including an alternative configuration for the expandable distal portion, which is shown in a first or non-expanded configuration.

FIG. 10 shows partial cross-sectional view of another example embodiment of a needle assembly 210 similar in form and function to needle assemblies 10 and 110 shown and described herein, wherein similarly named structures and/or similarly numbered structures may be similar in form and function as those discussed elsewhere herein. In this embodiment, however, the expandable distal portion 226 may be a non-coiled tubular member. Additionally, the entire elongated tubular member 222 may be of monolithic and/or unitary construction. In other words, the elongated tubular member 222, including the proximal body portion 24 and the expandable distal portion 226, may be a full length singular and/or monolithic structure, such as a tubular member, extrusion, coil, braid, mesh, or the like. In this particular embodiment shown, the elongated tubular member 222 may be a monolithic and/or singular tubular member and/or extrusion.

The expandable distal portion 226 has an inner surface 228 defining an inner lumen 230, and an outer surface 232. The expandable distal portion 226 has a wall 233 having a wall thickness that is defined between the inner surface 228 and the outer surface 232. The wall thickness of the expandable distal portion 226 is greater than the wall thickness of the proximal body portion 24. The expandable distal portion 226 may have an outer diameter D2 and an inner diameter D3. The expandable distal portion 26 may be configured to radially expand and/or contract such that it can shift between a first, radially non-expanded configuration and a second, radially expanded configuration, as will be discussed in more detail below and herein.

Figure 11:
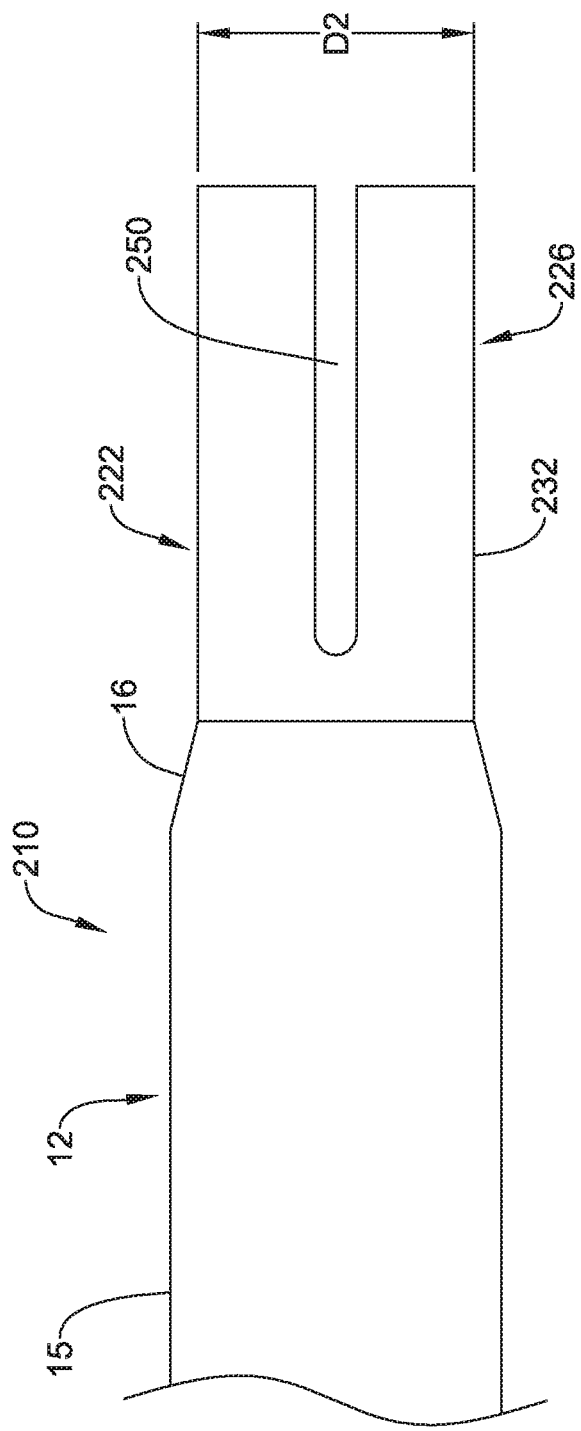
FIG. 11 is a partial side view of the example embodiment of FIG. 10.

FIG. 11 shows side view of the needle assembly 210. In the side view, it can be seen that the expandable distal portion 226 may include one or more expansion relief structures 250, such as one or more channels, slots, folds, cuts, material changes, durometer changes, or the like, formed, cut, built and/or otherwise disposed in and extending longitudinally along and/or in the wall 233. Such expansion relief structures 250 may allow for controlled and/or easier expansion of the monolithic and/or unitary expandable distal portion 226. For example, the expansion relief structures 250 may be designed and/or configured to preferentially expand and/or be more expandable than the remaining portions of the wall 233. The expandable distal portion 226 may include a single expansion relief structure 250 or may include a plurality of such expansion relief structures 250. If a plurality of expansion relief structures are used, they may be spaced apart radially from each other in any fashion as desired. For example, a plurality of expansion relief structures 250 may be spaced apart radially equally about the expandable distal portion 226 (e.g., two expansion relief structures spaced radially apart by 180 degrees, three expansion relief structures spaced radially apart by 120 degrees, four expansion relief structures spaced radially apart by 90 degrees, etc.), or may be spaced apart unequally radially about the expandable distal portion 226 (e.g. three expansion relief structures, with a first two spaced radially apart from each other by 40 degrees, and a third spaced apart from the first two by 160, etc.).

Similar to the other embodiments described herein, the expandable distal portion 226 is designed to shift between a first, radially non-expanded configuration, and a second, radially expanded configuration. FIGS. 10 an 11 show the expandable distal portion 226 in the first, non-expanded configuration, in which the expandable distal portion 226 has an outer diameter D2 that is the same as or less than the inner diameter D1 of the needle lumen 18. (as seen in FIG. 10). As such, in this first configuration, the needle 12, including the sharp distal tip 16, may be longitudinally moved over and/or about the expandable distal portion 226, and/or the expandable distal portion 226 may be moved within the needle 12 such that it is disposed within and/or movable within the needle lumen 18. In this first configuration, the sharp needle tip 16 may be considered to not be radially protected and/or guarded by the expandable distal portion 226, relative to when in the second expanded configuration.

In this particular embodiment, when in the first, non-expanded configuration, the elongated tubular member 222 may have a constant outer diameter along its length. For example, the outer diameter D2 of the expandable distal portion 26 may be equal to the outer diameter D5 the proximal body portion 24. Additionally, in this embodiment, when in the first, non-expanded configuration, the inner diameter of the elongated tubular member 222 may vary along its length. For example, the inner diameter D3 of the expandable distal portion 26 may be smaller than the inner diameter D4 of the proximal body portion 24. There may be a tapered transition in inner diameter and/or wall thickness of the elongated tubular member 222 between the proximal body portion 24 and the expandable distal portion 26.

Figure 12:
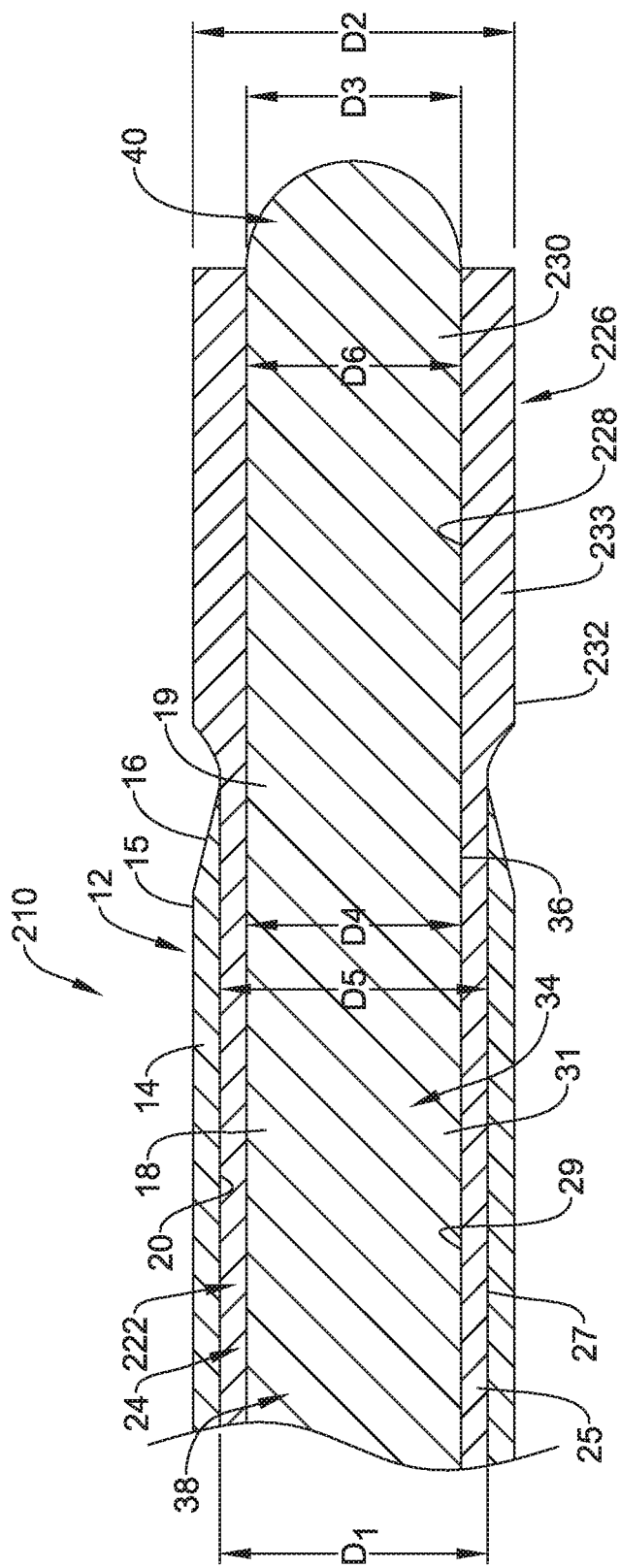
FIG. 12 is a partial cross-sectional side view of the example embodiment of FIG. 10, with the expandable distal portion shown in a second or expanded configuration, guarding the sharp distal tip of the needle.
Figure 13:
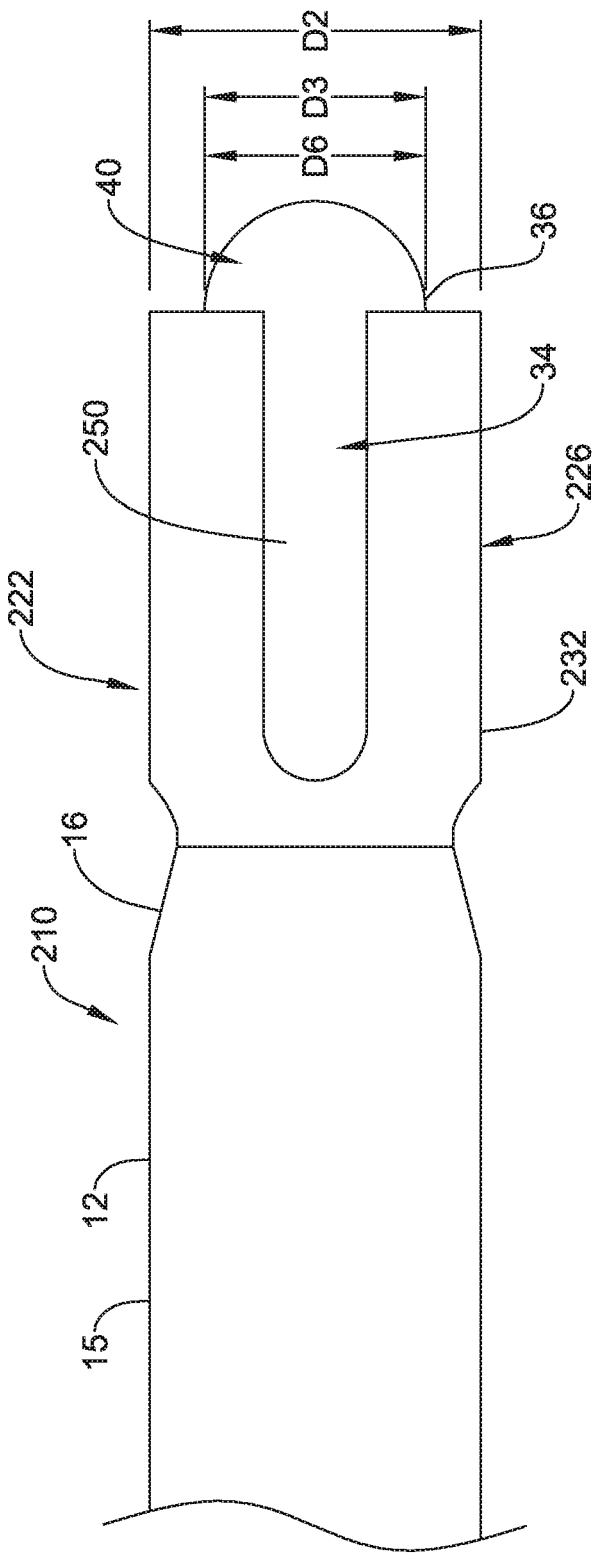
FIG. 13 is a partial side view of the example embodiment of FIG. 12, with the expandable distal portion shown in a second or expanded configuration, guarding the sharp distal tip of the needle.

FIG. 12 shows the expandable distal portion 226 in the second configuration, in which the expandable distal portion 226 has an outer diameter D2 that is larger than the inner diameter D1 of the needle lumen 18. The elongated inner member 34 has been moved longitudinally in a distal direction and forced into the inner lumen 230 of the expandable distal portion 226 with a predetermined amount of force, such that the outer surface 36 of the elongated inner member 34 engages and/or is engaged with the inner surface 228 of the expandable distal portion 226. Because the outer diameter D6 of the elongated inner member 34 is larger than the initial (e.g. non-expanded) inner diameter D3 of the expandable distal member 226, as the elongated inner member 34 is inserted therein, it forces the expandable distal portion 226 to expand radially. FIG. 13 shows a side view of the needle assembly 210 in the second, expanded configuration. As can be appreciated, the one or more expansion relief structures 250 may expand and/or open in response to the expansion force, allowing for better and/or more controlled and/or easier expansion of the monolithic and/or unitary expandable distal portion 226. The expansion relief structures 250 may be designed and/or configured to preferentially expand and/or be more expandable than the remaining portions of the wall 233.

Referring back to FIG. 12, this radial expansion thus increases both the inner diameter D3 and outer diameter D2 of the expandable distal portion 226 when in the second configuration relative to these diameters in the first, non-expanded configuration. As such, the expandable distal portion 226 when in this second, expanded configuration may have an outer diameter D2 that is configured such that it cannot fit within and/or be longitudinally movable within the needle lumen 18. The expandable distal portion 226 is disposed adjacent to the sharp distal tip 16, and now has a larger diameter D2, and thus may act to guard and/or protect the sharp distal tip 16. As such, in this configuration, the sharp distal tip 16 may be considered to be radially protected and/or guarded by the expandable distal portion 226.

Figure 14:
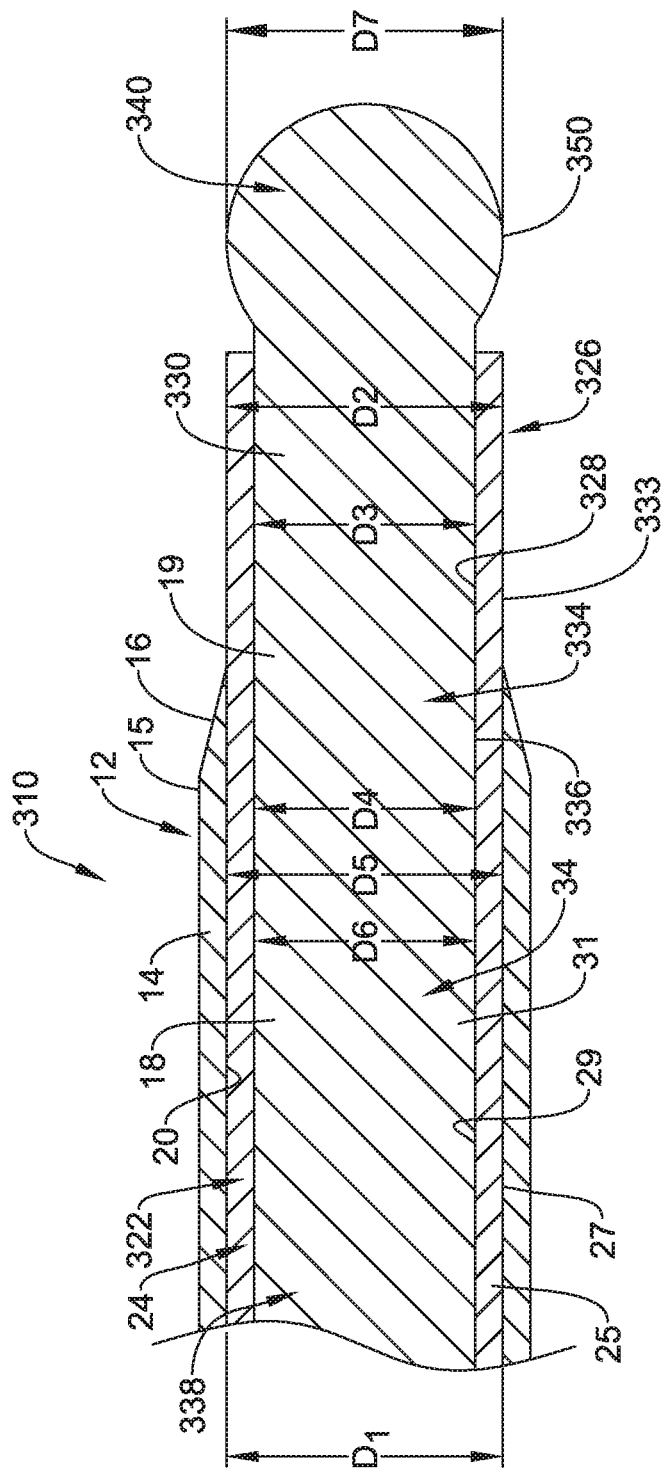
FIG. 14 is a partial cross-sectional side view of another example embodiment of a medical needle assembly including an alternative configuration for the expandable distal portion and the elongated inner member, wherein the expandable distal portion is shown in a first or non-expanded configuration.

FIG. 14 shows partial cross-sectional view of another example embodiment of a needle assembly 310 similar in form and function to needle assemblies 10, 110 and 210 shown and described herein, wherein similarly named structures and/or similarly numbered structures may be similar in form and function to those discussed elsewhere herein. In this embodiment, the elongated tubular member 322 may include a constant wall thickness along its length. The elongated tubular member 322 includes the proximal body portion 24 and the expandable distal portion 326. The proximal body portion 24 has an outer surface 27 and an inner surface 29, which defines an inner lumen 31. The proximal body portion 24 has a wall 25 having a first wall thickness which is defined between the outer surface 27 and the inner surface 29. The expandable distal portion 326 has an inner surface 328 defining an inner lumen 330, and an outer surface 332. The expandable distal portion 326 has a wall 333 having a wall thickness that is defined between the inner surface 328 and the outer surface 332. The wall thickness of the expandable distal portion 326 is the same as the wall thickness of the proximal body portion 24. As in other embodiments herein, the expandable distal portion 26 may be configured to radially expand and/or contract such that it can shift between a first, radially non-expanded configuration and a second, radially expanded configuration. The proximal body portion 24 may have an outer diameter D5 and an inner diameter D4. The expandable distal portion 326 may have an outer diameter D2 and an inner diameter D3. As can be appreciated, because of the constant wall thickness along the length of the elongated tubular member 322, when the expandable distal portion 326 is in the first, non-expanded configuration, the outer diameter D2 may equal to the outer diameter D5, and the inner diameter D3 may equal the inner diameter D4.

The elongated inner member 334 in this embodiment includes different and/or varying outer diameters along its length. The elongated inner member 334 includes a proximal segment 338 and a distal segment 340. The proximal segment 338 has an outer surface 336 and an outer diameter D6, and the distal segment 340 has an outer surface 350 and an outer diameter D7 that is greater than the outer diameter D6 of proximal segment 338. The outer diameter D6 of the proximal segment 338 may be sized and/or configured such that the proximal segment 338 of the elongated inner member 334 may fit within, and/or be longitudinally movable within, the elongated tubular member 322. For example, the proximal segment 338 of the elongated inner member 334 may be sized and/or configured to fit within and/or be longitudinally movable within the inner lumen 31 of the proximal body portion 24 and the inner lumen 330 of the expandable distal portion 326. For example, the elongated inner member 334 may have an outer diameter D6 that is less than the inner diameter D4 of the proximal body portion 24 and less than the inner diameter D3 of the distal expandable portion 336, such that the proximal segment 338 of the elongated inner member 334 may be disposed within and/or longitudinally movable within the inner lumens 31 and 330. The outer diameter D7 of the distal segment 340, however, may be greater than the inner diameter D3 of the expandable distal portion 326, and may also be greater than the inner diameter D4 of the proximal body portion 24.

As shown in FIG. 14, the elongated inner member 334 may be at least partially disposed within the elongated tubular member 322 such that the proximal segment 338 is disposed within the inner lumens 31 and 330, and the distal segment 340 extends distally beyond the expandable distal portion 326. The elongated inner member 334 may be configured and/or arranged to shift the expandable distal portion 326 between the first, or radially non-expanded configuration and the second, or radially expanded configuration. For example, distal segment 340 including the outer diameter D7 that is larger than the inner diameter D3 of the expandable distal portion 326 when in the first, or radially non-expanded configuration may be used to expand the expandable distal portion 326.

FIG. 14 shows the expandable distal portion 326 in the first, non-expanded configuration, in which the expandable distal portion 326 has an outer diameter D2 that is the same as or less than the inner diameter D1 of the needle lumen 18. As such, in this first configuration, the needle 12, including the sharp distal tip 16, may be longitudinally moved over and/or about the expandable distal portion 326, and/or the expandable distal portion 326 may be moved within the needle 12 such that it is disposed within and/or movable within the needle lumen 18. Similarly, the outer diameter D7 of the distal segment 340 of the elongated inner member 334 may be less than the inner diameter D1 of the needle lumen 18. As such, the needle 12 may similarly be longitudinally moved over and/or about the distal segment 340 of the elongated inner member 334, and/or the distal segment 340 of the elongated inner member 334 may be moved within the needle 12 such that it is disposed within and/or movable within the needle lumen 18. In this first configuration, the sharp needle tip 16 may be considered to not be radially protected and/or guarded by the expandable distal portion 326, relative to when in the second expanded configuration.

Figure 15:
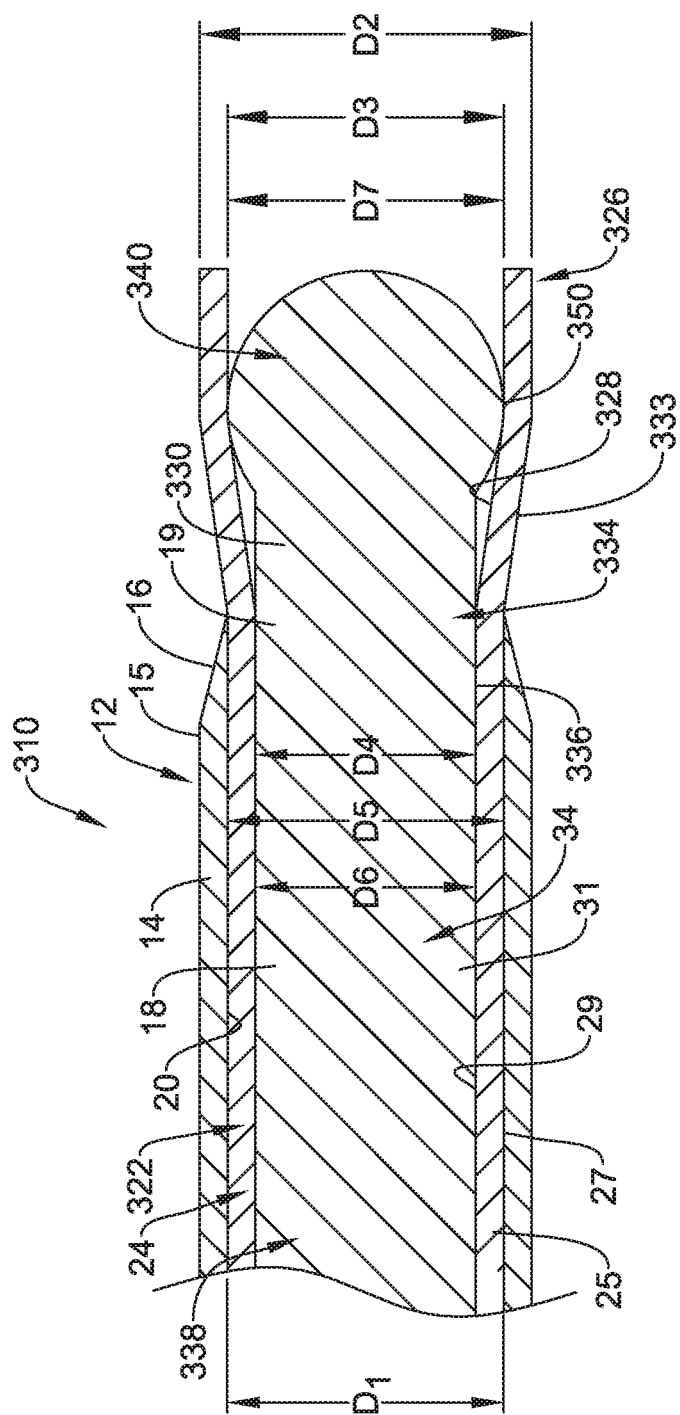
FIG. 15 is a partial cross-sectional side view of the example embodiment of FIG. 14, with the expandable distal portion in a second or expanded configuration, guarding the sharp distal tip of the needle.

FIG. 15 shows the expandable distal portion 326 in the second configuration, in which the expandable distal portion 326 has an outer diameter D2 that is larger than the inner diameter D1 of the needle lumen 18. The elongated inner member 334 has been moved longitudinally in a proximal direction and forced into the inner lumen 330 of the expandable distal portion 326 with a predetermined amount of force, such that the outer surface 350 of the distal portion 340 of the elongated inner member 334 engages and/or is engaged with the inner surface 328 of the expandable distal portion 326. Because the outer diameter D7 of the elongated inner member 334 is larger than the initial (e.g. non-expanded) inner diameter D3 of the expandable distal member 326, as the elongated inner member 334 is inserted therein, it forces the expandable distal portion 326 to expand radially. As can be appreciated, the expandable distal member 326 may include one or more expansion relief structures, as discussed elsewhere herein, that may expand and/or open in response to the expansion force, allowing for better and/or more controlled and/or easier expansion of the expandable distal portion 326. Additionally or alternatively, the expandable distal member 326 may include structure and/or materials that allow it to expand.

This radial expansion thus increases both the inner diameter D3 and outer diameter D2 of the expandable distal portion 326 when in the second configuration relative to these diameters in the first, non-expanded configuration. As such, the expandable distal portion 326 when in this second, expanded configuration may have an outer diameter D2 that is configured such that it cannot fit within and/or be longitudinally movable within the needle lumen 18. The expandable distal portion 326 is disposed adjacent to the sharp distal tip 16, and now has a larger diameter D2, and thus may act to guard and/or protect the sharp distal tip 16. As such, in this configuration, the sharp distal tip 16 may be considered to be radially protected and/or guarded by the expandable distal portion 326.

Figure 16:
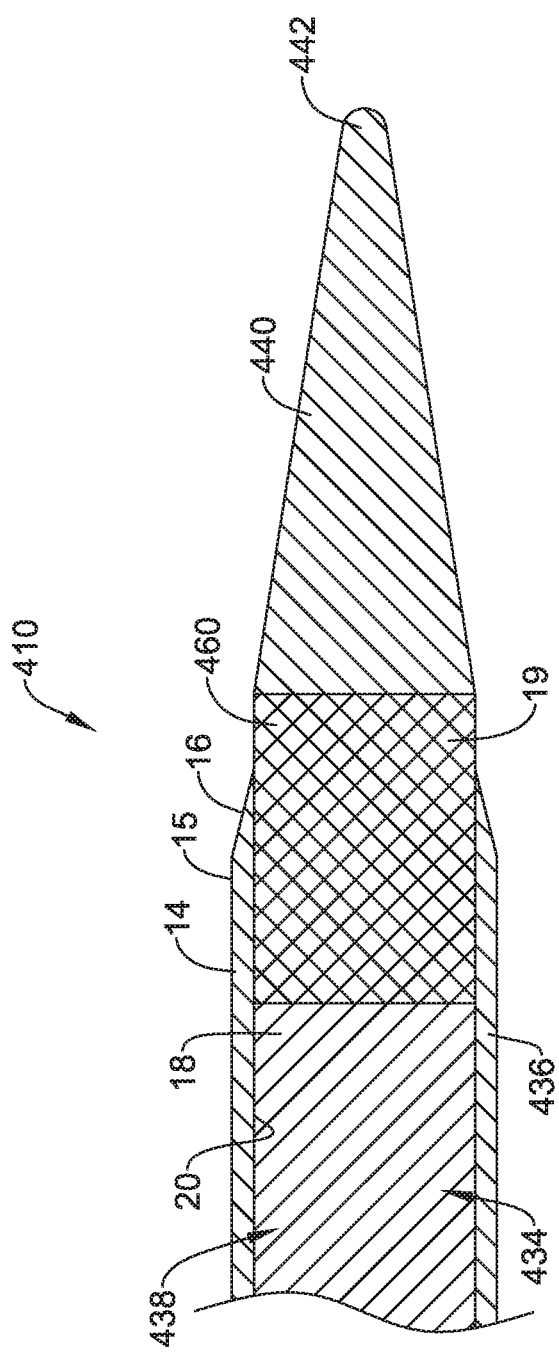
FIG. 16 is a partial cross-sectional side view of another example embodiment of a medical needle assembly including a needle having a sharp distal tip, and an elongate inner member disposed within the needle and including a rigid section disposed adjacent the sharp distal tip and including a blunt distal tip.

FIG. 16 shows partial cross-sectional view of an alternative example configuration for a medical needle assembly 410. Similar to the embodiments above, the medical needle assembly 410 includes a needle 12 having a needle body 14 defining a sharp distal tip 16. The needle body 14 has an outer surface 15, an inner surface 20, and defines a needle lumen 18 having an inner diameter. The sharp distal tip 16 defines a distal needle opening 19 into the needle lumen 18. The needle 12 may be of any of a wide variety of medical needles, for example, any of those already discussed herein.

In this embodiment, the needle assembly 410 includes an elongated stylet 434. The stylet includes a proximal segment 438, a distal segment 440, and an intermediate segment 460 disposed between the proximal and distal segments. The distal segment 440 includes a rounded blunt tip 442.

The stylet 443 may include a stiffness profile that varies along at least a portion of the length of the stylet 434. For example, the distal segment 440 includes an elongated tapering profile, wherein the diameter of the distal segment 440 decreases as it extends distally. As such, the distal segment 440 may be less stiff (e.g. more flexible) adjacent the tip 442, and gradually becomes stiffer (e.g. less flexible) as it extends proximally, with the stiffest portion disposed adjacent the intermediate segment 460. The intermediate segment 460 may be stiffer (e.g. less flexible) than the distal segment 440, for example, due to its larger diameter. The proximal segment 438 may also be stiffer (e.g. less flexible) than the distal segment 440, for example, due to its larger diameter. The proximal segment 438 and the intermediate segment 440 may be generally the same stiffness, for example, due to their common diameter. Additionally, or alternatively, the stylet 443 may include the use of different materials, such as different metals or polymers, with differing stiffness or durometers along the length thereof to achieve stiffness profile variations. For example, intermediate segment 460 may include a metal or polymer with higher stiffness or durometer, while the distal segment 440 may include a metal or polymer with lower stiffness or durometer. Similarly, the proximal segment 438 may include a metal or polymer with higher stiffness or durometer relative to the material used in the distal segment 440. The proximal segment 438 and the intermediate segment 440 may be generally the same stiffness through the use of similar stiffness materials, or may vary in stiffness from one another, for example, through the use of materials with varying stiffness. In some embodiments, the proximal segment 438 may be stiffer than the intermediate segment 440, while in other embodiments, the proximal segment 438 may be less stiff than the intermediate segment 440, or they may be the same stiffness, as desired.

Furthermore, as shown in FIG. 16, the tapered distal segment 440 may extend distally beyond the intermediate segment for a significant length. This long length distal segment 440 provides for a longer taper, and a more gradual variation in the stiffness profile. Additionally, this long distal segment 440 may aid in navigation and/or in helping to guard or protect the sharp needle tip 16 from undesirably contacting a delivery device and/or anatomy during navigation, as discussed in more detail below. In some embodiments, the tapered distal segment 440 has a length in the range of about 1 to about 10 cm.

As may also be appreciated, there is a tight tolerance between the outer surface 436 of stylet and the inner surface 20 of the needle 12. There is very little or no gap between the inner surface 20 of the needle 12 and the outer surface 436 of stylet.

The stylet 434 is disposed within the needle 12 such that the rigid intermediate segment 460 is disposed under and/or within the sharp distal tip 16 of the needle 12, and the tapered distal segment 440 extends distally beyond the sharp distal tip 16 and the rigid intermediate segment 460. In other words, the sharp distal tip 16 of the needle is disposed about and/or around the rigid intermediate segment 460, and/or surrounds the rigid intermediate segment 460. As such, the rigid intermediate segment 460 rigidly supports the sharp distal tip 16 of the needle, and thus reduces the likelihood that needle will flex and/or bend away from the stylet 434 when force is applied, for example, during navigation. As such, it is less likely that a gap would be created between the stylet 434 and the sharp distal tip 16, and therefore less likely that the sharp need tip 16 would undesirably skive, scrape, puncture or become embedded or stuck in the delivery device or in the anatomy during navigation.

Additionally, the long distal segment 440 may aid in navigation and/or in helping to guard or protect the sharp needle tip from undesirably contacting a delivery device and/or the anatomy during such navigation. Because of the long length of the tapered distal segment 440, the blunt tip 442 is spaced a significant distance distally from the sharp need tip 16. During navigation, especially though tight and/or tortuous curves, the blunt tip 442 will be leading, and will generally be the first structure of the assembly 410 to make contact with the delivery device and/or antomy. The long tapered distal segment 440 may help to space the sharp need tip 16 from this contact with the delivery device and/or tissue and may help to dissipate any bending force applied to the stylet 434. For example, the long distal segment 440 having a tapered stiffness may guide the needle during navigation, for example, through tight curves. As such, the long tapered distal segment 440, in conjunction with the rigid intermediate segment 460, may help to reduce and/or prevent separation of the needle 12 from the stylet 434, thus making it less likely that a gap would be created between the stylet 434 and the sharp needle tip 16, and therefore less likely that the sharp needle tip 16 would undesirably skive, scrape, puncture or become embedded or stuck in the delivery device or in the anatomy during navigation.

The materials that can be used for the various devices, assemblies and components disclosed herein may include those commonly associated with medical devices. For example, the needle, expandable medical device, elongated tubular member, expandable distal portion, proximal body portion, elongated inner member, stylet, and/or any of the components thereof or of any of medical needle assemblies disclosed herein may be made from a metal, metal alloy, polymer, a metal-polymer composite, ceramics, combinations thereof, and the like, or other suitable material or composites of materials. Some examples of suitable metals and metal alloys include stainless steel, such as 304V, 304L, 316LV, and 17-7 stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), thermoplastic polyurethane (for example, PELLETHANE®), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

The needle, expandable medical device, elongated tubular member, expandable distal portion, proximal body portion, elongated inner member, stylet, and/or any of the components thereof or of any of medical needle assemblies disclosed herein may include the use of different metals or polymers with differing stiffness or durometers along the length thereof. For example, a more proximal section of any of the components, devices or assemblies disclosed herein may include a metal or polymer with higher stiffness or durometer and a more distal section may include a metal or polymer with lower stiffness or durometer. Any of the components, devices or assemblies disclosed herein may include or be made of one or more layers of materials. For example, a plurality or layers of differing material may be used to form all or portions of the any of the components, devices or assemblies disclosed herein. Any of the components, devices or assemblies disclosed herein may also include and/or be entirely made of a reinforcement member, such as a braid, coil, mesh, or the like.

In at least some embodiments, portions or all of the needle, expandable medical device, elongated tubular member, expandable distal portion, proximal body portion, elongated inner member, stylet, and/or any of the components thereof or of any of medical needle assemblies disclosed herein may be doped with, made of, or otherwise include a radiopaque material. Radiopaque materials are understood to be materials capable of producing a relatively bright image on a fluoroscopy screen or another imaging technique during a medical procedure. This relatively bright image aids the user of the guide extension catheter in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design to achieve the same result.

In some embodiments, a degree of Magnetic Resonance Imaging (MRI) compatibility is imparted into the design. For example, the needle, expandable medical device, elongated tubular member, expandable distal portion, proximal body portion, elongated inner member, stylet, and/or any of the components thereof or of any of medical needle assemblies disclosed herein or portions thereof, may be made of a material that does not substantially distort the image and create substantial artifacts (e.g., gaps in the image). Certain ferromagnetic materials, for example, may not be suitable because they may create artifacts in an MRI image. Any of the components, devices or assemblies disclosed herein, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical needle assembly comprising:
a needle having a needle body including a sharp distal tip and having a needle lumen defining an inner diameter;
an elongated tubular member configured to be at least partially disposed within the needle lumen and including an expandable distal portion having an inner lumen defining an inner surface, wherein the expandable distal portion is designed to shift between a first configuration in which the expandable distal portion has an outer diameter that is the same as or less than the inner diameter of the needle lumen and a second configuration in which the expandable distal portion has an outer diameter that is greater than the inner diameter of the needle lumen; and
an elongated inner member configured to shift the expandable distal portion from the first configuration to the second configuration;
wherein the elongated inner member defines an outer surface, wherein the outer surface of the elongated inner member disengages from the inner surface of the expandable distal portion to shift the expandable distal portion from the second configuration to the first configuration.

2. The medical needle assembly of claim 1, wherein the expandable distal portion is disposed distal of and adjacent to the sharp distal tip when in the second configuration such that the expandable distal portion guards the sharp distal tip of the needle.

3. The medical needle assembly of claim 1, wherein the outer surface of the elongated inner member engages the inner surface of the expandable distal portion to shift the expandable distal portion from the first configuration to the second configuration.

4. The medical needle assembly of claim 1, wherein the expandable distal portion has an inner diameter, and the elongated inner member has an outer diameter, and when in the first configuration, the outer diameter of the elongated inner member is greater than the inner diameter of the expandable distal portion.

5. The medical needle assembly of claim 4, wherein the inner member includes a proximal segment and a distal segment, and the distal segment includes the outer diameter that is greater than the inner diameter of the expandable distal portion, and the proximal segment includes an outer diameter that is less than the outer diameter of the distal segment.

6. The medical needle assembly of claim 1, wherein the elongated tubular member includes a proximal body portion having a first wall thickness, and the distal expandable portion has a second wall thickness that is greater than the first wall thickness.

7. The medical needle assembly of claim 1, wherein the elongated tubular member comprises a coil.

8. The medical needle assembly of claim 1, wherein the distal expandable portion comprises a coil.

9. The medical needle assembly of claim 1, wherein the distal expandable portion comprises a tubular body including an expansion relief slot formed therein.

10. An expandable stylet for guarding a sharp distal tip of a needle defining a lumen, the expandable stylet comprising:
an elongated tubular member including a body portion configured to be at least partially disposed within the needle lumen, and an expandable distal portion defining an inner lumen including an inner surface, wherein the expandable distal portion is designed to shift between a first configuration in which the expandable distal portion has an outer diameter that is the same or less than the inner diameter of the needle lumen and a second configuration in which the expandable distal portion has an outer diameter that is greater than the inner diameter of the needle lumen and is configured to guard the sharp distal tip of the needle; and an elongated inner member configured to be at least partially disposed within the inner lumen of the elongated tubular member and being configured to shift the expandable distal portion between the first configuration and the second configuration;

wherein the elongated inner member defines an outer surface, wherein the outer surface of the elongated inner member disengages from the inner surface of the expandable distal portion to shift the expandable distal portion from the second configuration to the first configuration.

11. The expandable stylet of claim 10, wherein when in the second configuration the outer diameter of the expandable distal portion is greater than an outer diameter of the body portion.

12. The expandable stylet of claim 10, wherein the outer surface of the elongated inner member engages the inner surface of the expandable distal portion to shift the expandable distal portion from the first configuration to the second configuration.

13. The expandable stylet of claim 10, wherein the expandable distal portion has an inner diameter, and the elongated inner member has an outer diameter, and when in the first configuration, the outer diameter of the elongated inner member is greater than the inner diameter of the expandable distal portion.

14. The expandable stylet of claim 13, wherein the inner member includes a proximal segment and a distal segment, and the distal segment includes the outer diameter that is greater than the inner diameter of the expandable distal portion, and the proximal segment includes an outer diameter that is less than the outer diameter of the distal segment.

15. The expandable stylet of claim 10, wherein the elongated tubular member includes a proximal body portion having a first wall thickness, and the distal expandable portion has a second wall thickness that is greater than the first wall thickness.

16. A method of guarding a sharp tip of a needle having a needle lumen, the method comprising:

disposing an elongated tubular member having an expandable distal portion within the needle lumen such that the expandable distal portion is distal of the sharp tip, the expandable distal portion being in a first configuration in which the expandable distal portion has an outer diameter that is the same or less than an inner diameter of the needle lumen;

shifting the expandable distal portion to a second configuration in which the expandable distal portion has an outer diameter that is greater than the inner diameter of the needle lumen, wherein an elongated inner member is used to shift the expandable distal portion from the first configuration to the second configuration;

wherein the elongated inner member defines an outer surface and the expandable distal portion has an inner lumen defining an inner surface, wherein shifting the expandable distal portion from the first configuration to the second configuration includes engaging the outer surface of the elongated inner member with the inner surface of the expandable distal portion such that the outer diameter of the expandable distal portion increases; and shifting the expandable distal portion from the second configuration to the first configuration by disengaging the outer surface of the elongated inner member from the inner surface of the expandable distal portion such that the outer diameter of the expandable distal portion decreases.

\* \* \* \* \*